United States Patent
Villain et al.

(10) Patent No.: US 11,819,664 B2
(45) Date of Patent: Nov. 21, 2023

(54) MIXING NOZZLE, APPLICATION DEVICE, KIT AND METHOD USING THE MIXING NOZZLE OR APPLICATION DEVICE

(71) Applicant: Merz Pharma GmbH & Co. KGaA, Frankfurt am Main (DE)

(72) Inventors: Franck Villain, Paris (FR); Uwe Wortmann, Marburg (DE); Norbert Kaspers, Schnaittenbach (DE); Johannes Egger, Munich (DE); Thomas Sowden Reinhold, Bad Oeynhausen (DE); Guido Popp, Frankfurt (DE); Michael Kunz, Muenster (DE); Jonathan Mason, Hertfordshire (GB)

(73) Assignee: MERZ PHARMA GMBH & CO. KGAA, Frankfurt (DE)

( * ) Notice: Subject to any disclaimer, the term of this patent is extended or adjusted under 35 U.S.C. 154(b) by 112 days.

(21) Appl. No.: 16/621,533

(22) PCT Filed: Jun. 13, 2018

(86) PCT No.: PCT/EP2018/065642
§ 371 (c)(1),
(2) Date: Dec. 11, 2019

(87) PCT Pub. No.: WO2018/229117
PCT Pub. Date: Dec. 20, 2018

(65) Prior Publication Data
US 2020/0171243 A1 Jun. 4, 2020

(30) Foreign Application Priority Data

Jun. 13, 2017 (EP) ..................... 17175858
Dec. 21, 2017 (EP) ..................... 17209718

(51) Int. Cl.
*A61M 5/24* (2006.01)
*A61M 5/19* (2006.01)
(Continued)

(52) U.S. Cl.
CPC ............ *A61M 5/2448* (2013.01); *A61M 5/19* (2013.01); *A61M 5/3134* (2013.01);
(Continued)

(58) Field of Classification Search
CPC .... A61M 5/2448; A61M 5/19; A61M 5/3134; A61M 5/347; A61M 2202/0078
See application file for complete search history.

(56) References Cited

U.S. PATENT DOCUMENTS 6,479,468 B1 * 11/2002 Hedlund .............. A61K 31/718
514/60
7,883,501 B2 2/2011 McIntosh et al.
(Continued)

FOREIGN PATENT DOCUMENTS

DE 202006004738 U1 6/2006
DE 102013103552 A1 10/2014
(Continued)

OTHER PUBLICATIONS

PCT International Search Report for PCT/EP2018/065642, dated Sep. 10, 2018.

*Primary Examiner* — Bradley J Osinski
(74) *Attorney, Agent, or Firm* — MCBEE MOORE & VANIK IP, LLC; Susan McBee; Kurt Buechle

(57) ABSTRACT

The present invention generally relates to a mixing nozzle (12) for mixing at least two liquid compositions such as a first liquid composition and a second liquid composition. The mixing nozzle (10) is configured to be coupled to a body (11) of a multi-component application device (10), in particular to a body (11) of a two-component syringe assembly,
(Continued)

for injection of a liquid composition, which body (11) is configured to separately store said at least two solutions. The present invention further relates to a multi-component application device (10) comprising said mixing nozzle (12) and to a kit comprising said mixing nozzle (12) or said application device (10). Furthermore, the present invention relates to a method using said application device or said kit, for example for replacing or filling a biological tissue or increasing the volume of a biological tissue.

16 Claims, 21 Drawing Sheets

(51) Int. Cl.
*A61M 5/31* (2006.01)
*A61M 5/34* (2006.01)

(52) U.S. Cl.
CPC ..... *A61M 5/347* (2013.01); *A61M 2202/0007* (2013.01); *A61M 2202/0078* (2013.01)

(56) References Cited

U.S. PATENT DOCUMENTS

| | | | |
|---|---|---|---|
| 2005/0243647 A1 | 11/2005 | Gray et al. | |
| 2010/0318063 A1* | 12/2010 | Soll | A61M 5/19 604/518 |
| 2011/0139821 A1* | 6/2011 | Greter | A61B 17/00491 222/145.5 |
| 2015/0335397 A1* | 11/2015 | Muller | A61C 9/0026 433/89 |

FOREIGN PATENT DOCUMENTS

| | | |
|---|---|---|
| EP | 0800361 B1 | 5/1999 |
| WO | 2008009143 A1 | 1/2008 |

* cited by examiner

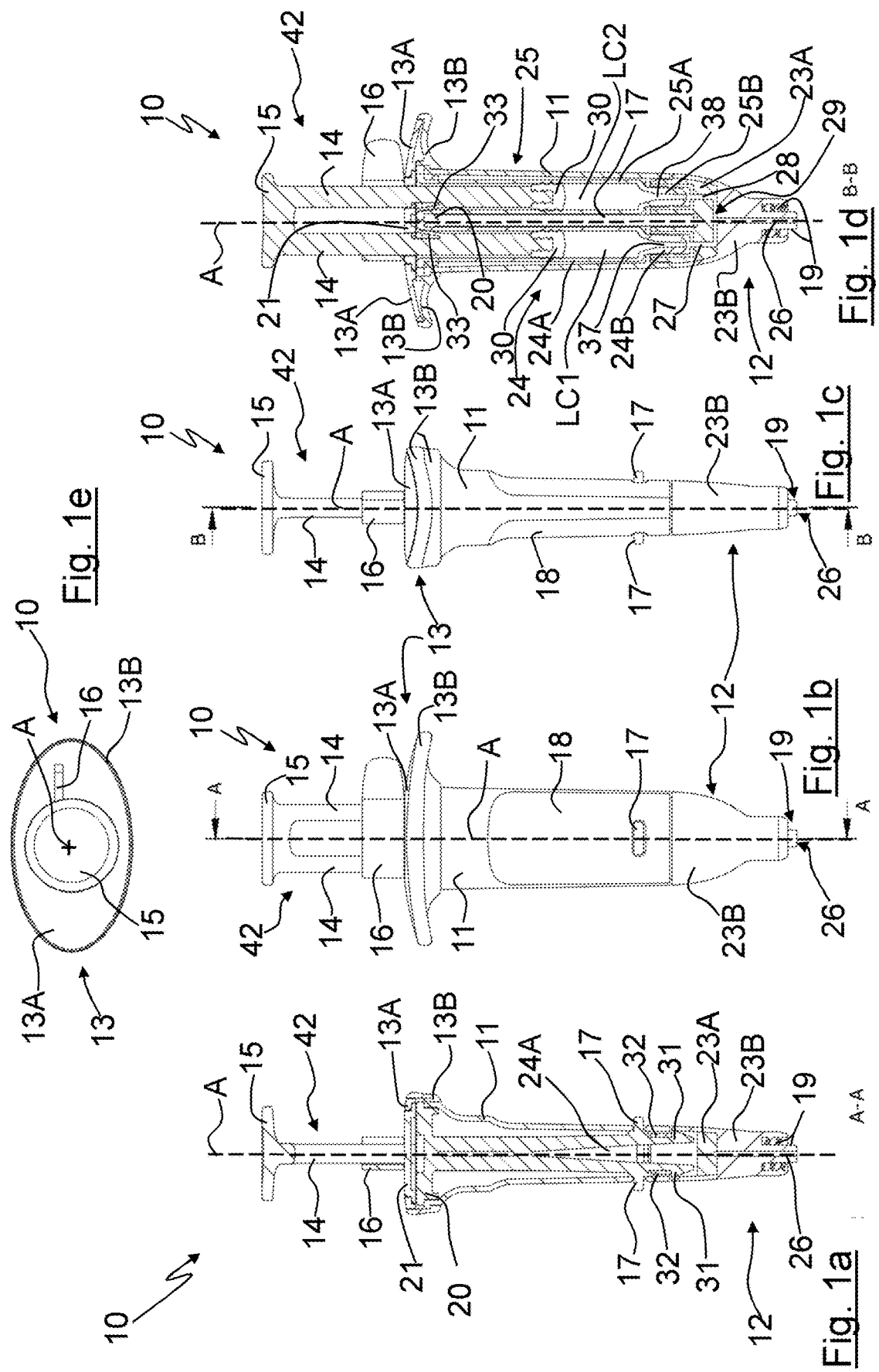

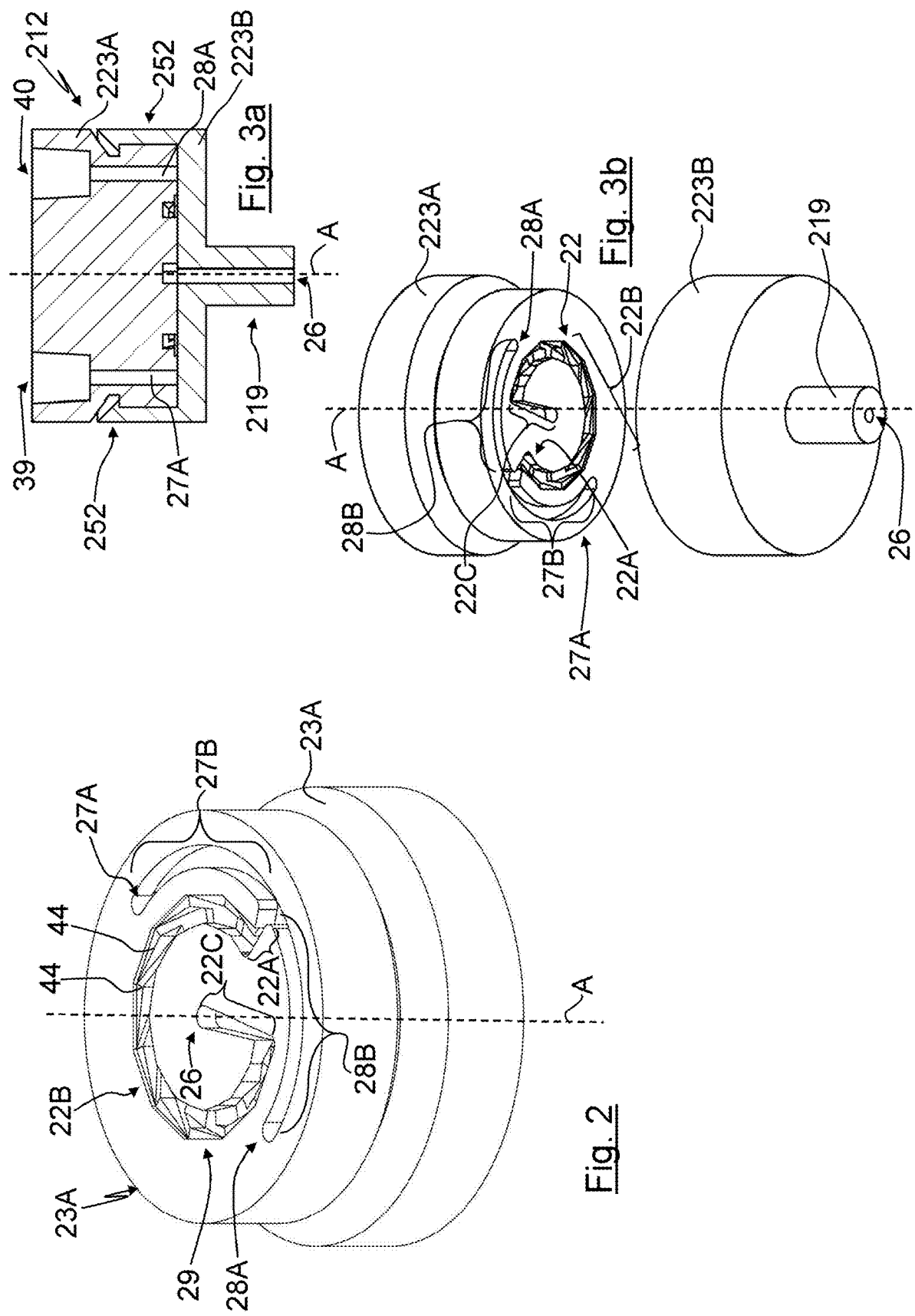

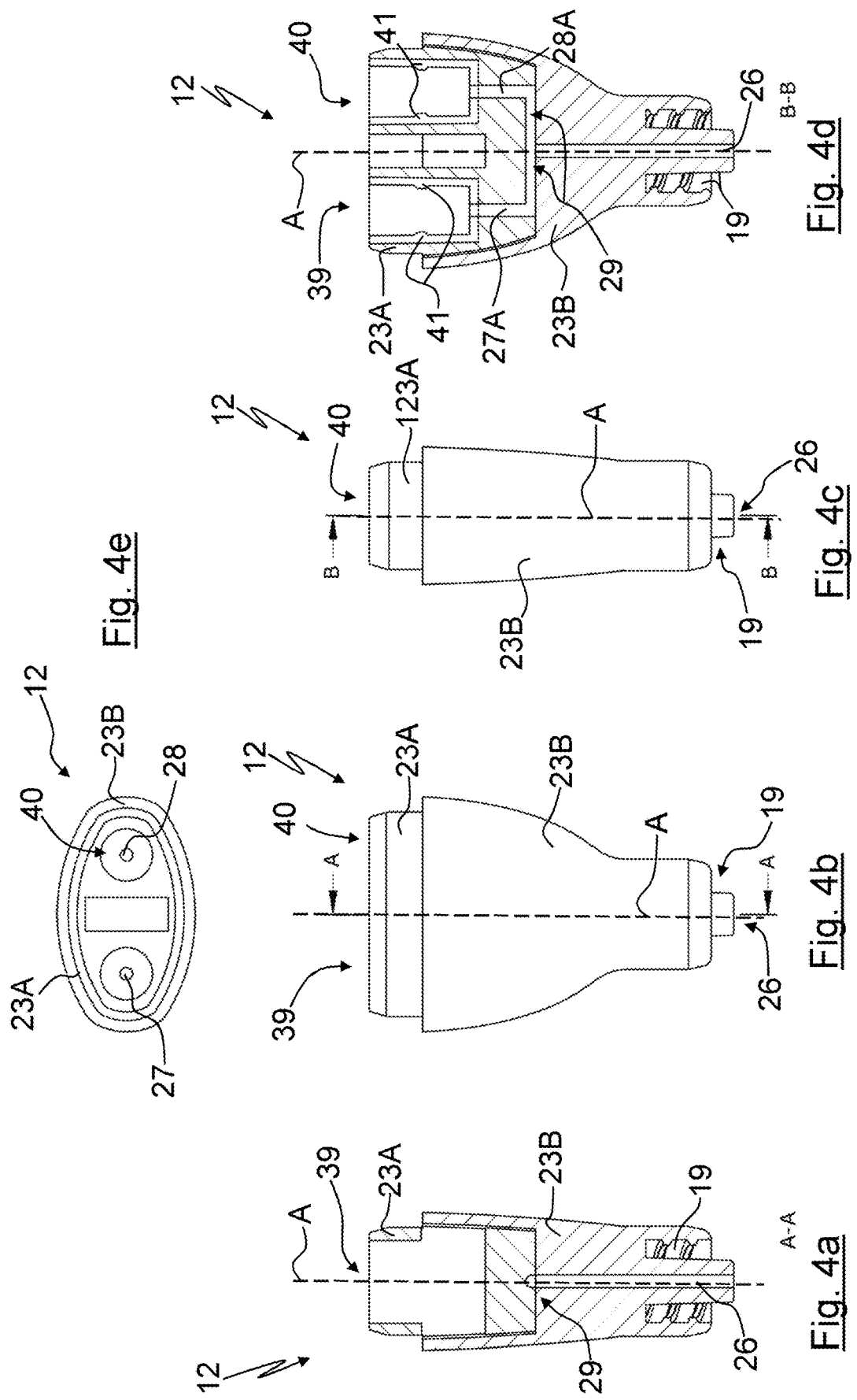

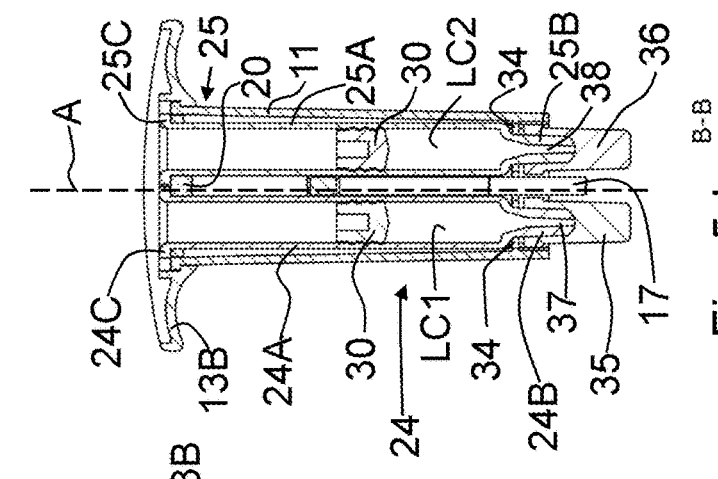
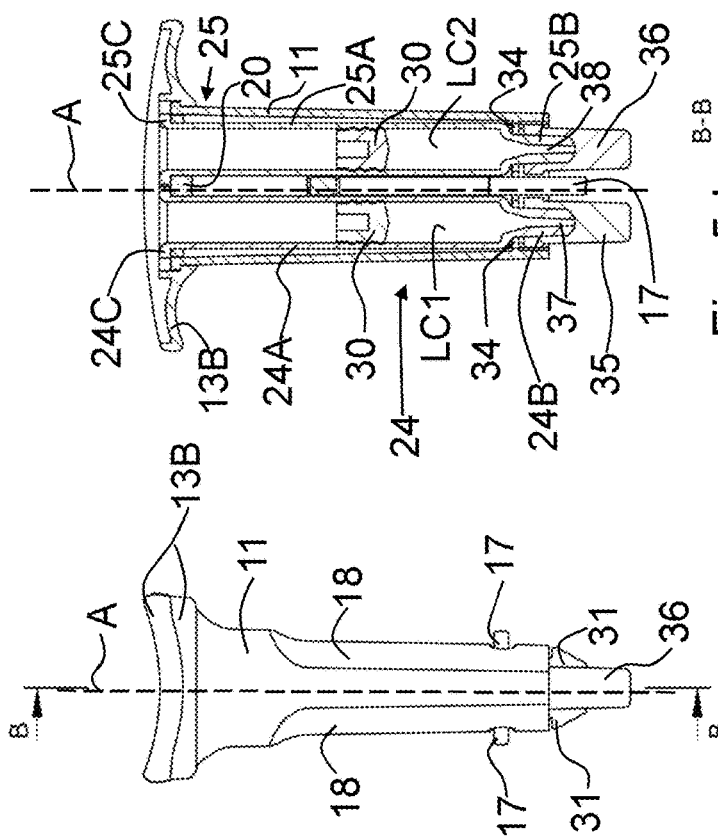
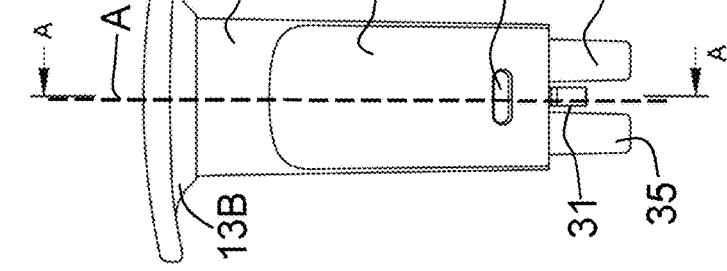
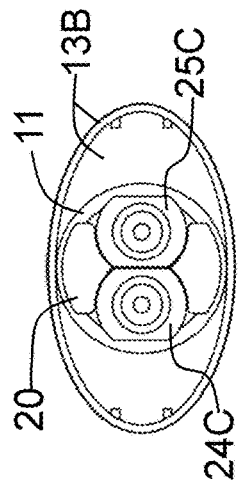
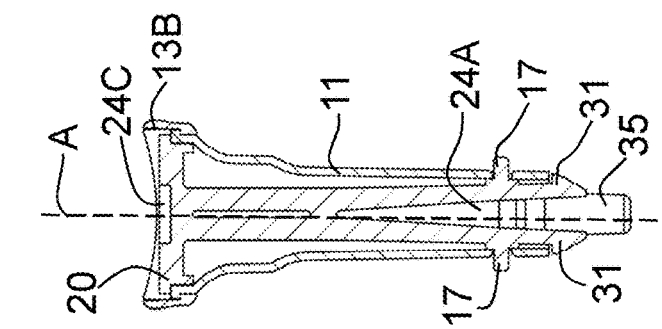

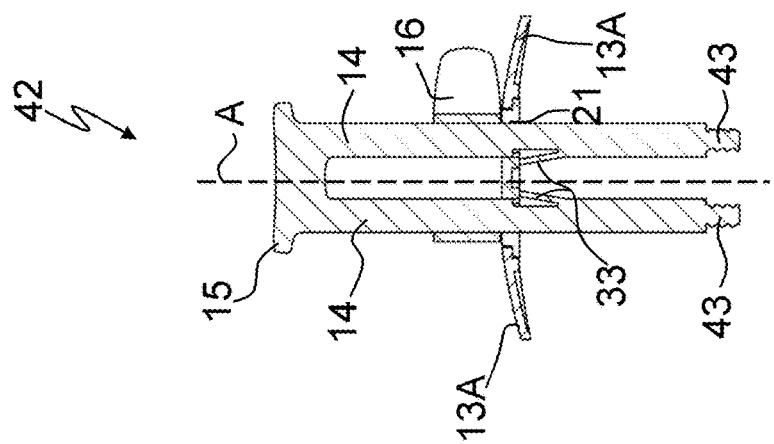
Fig. 6d
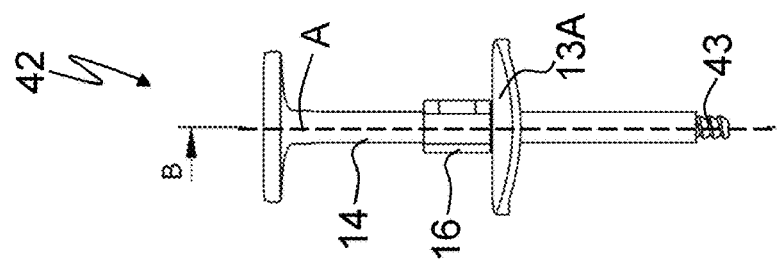
Fig. 6c
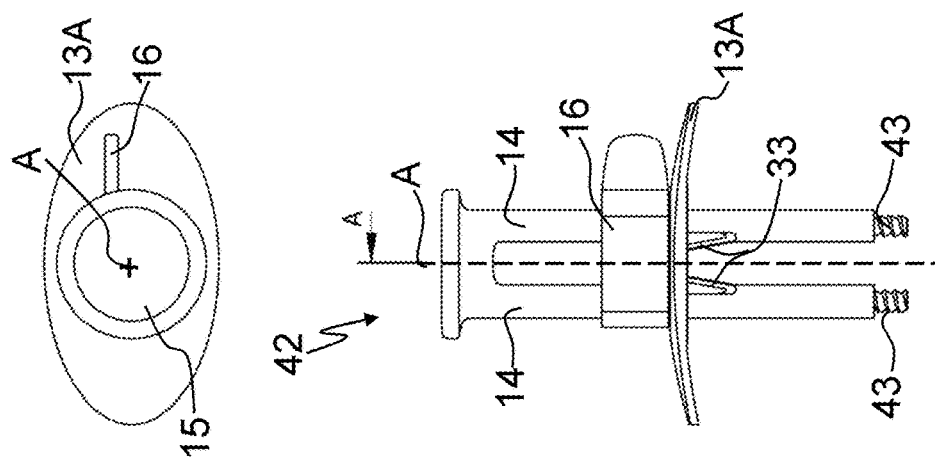
Fig. 6e
Fig. 6b
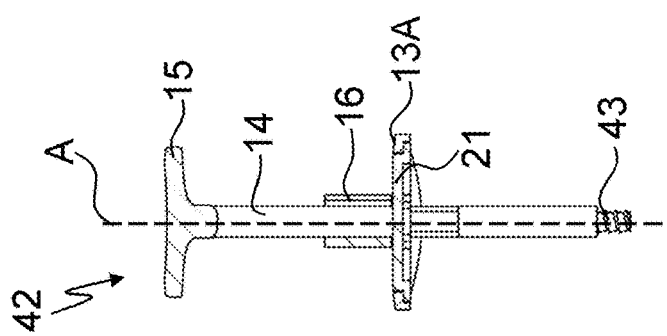
Fig. 6a

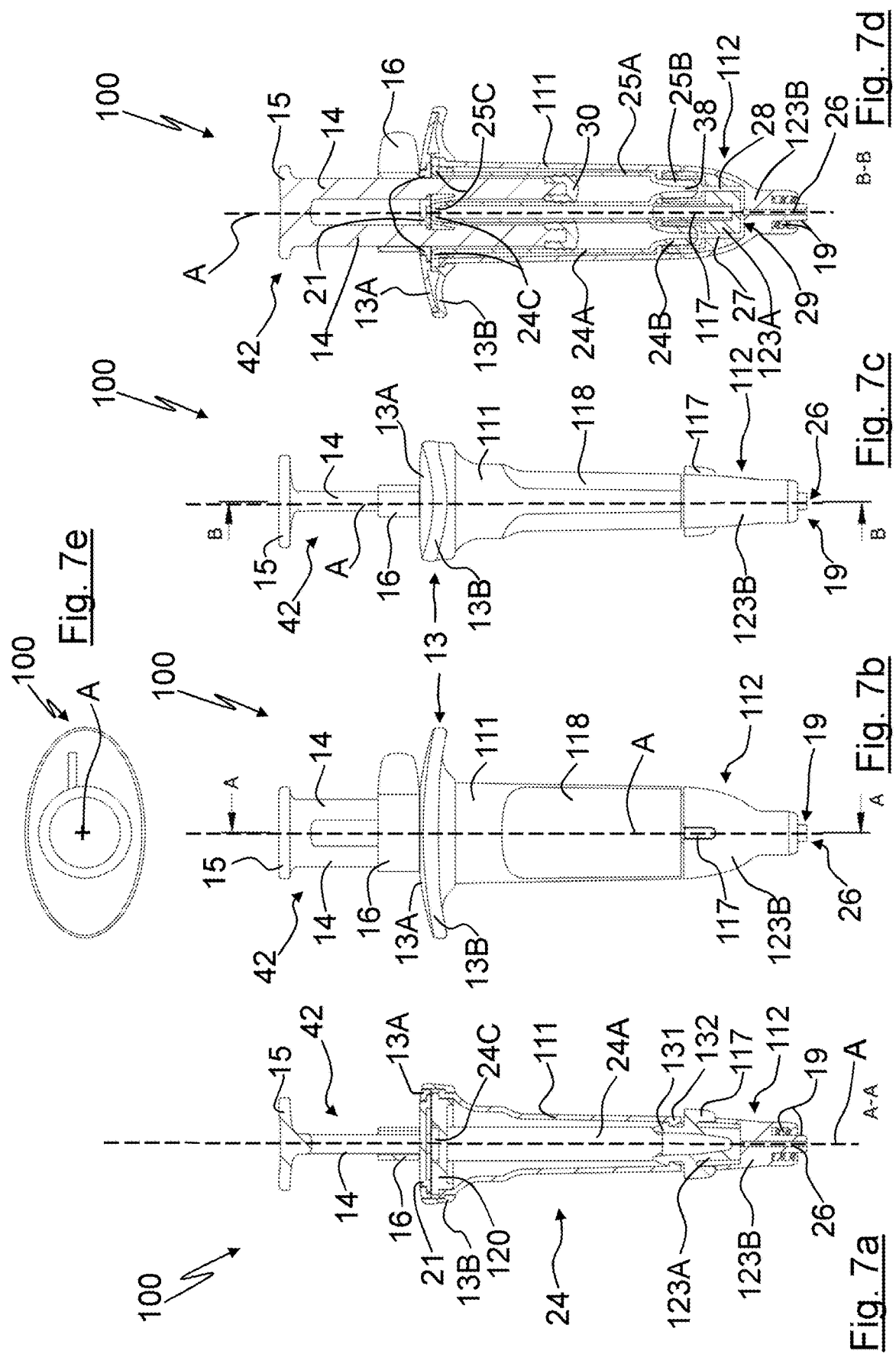

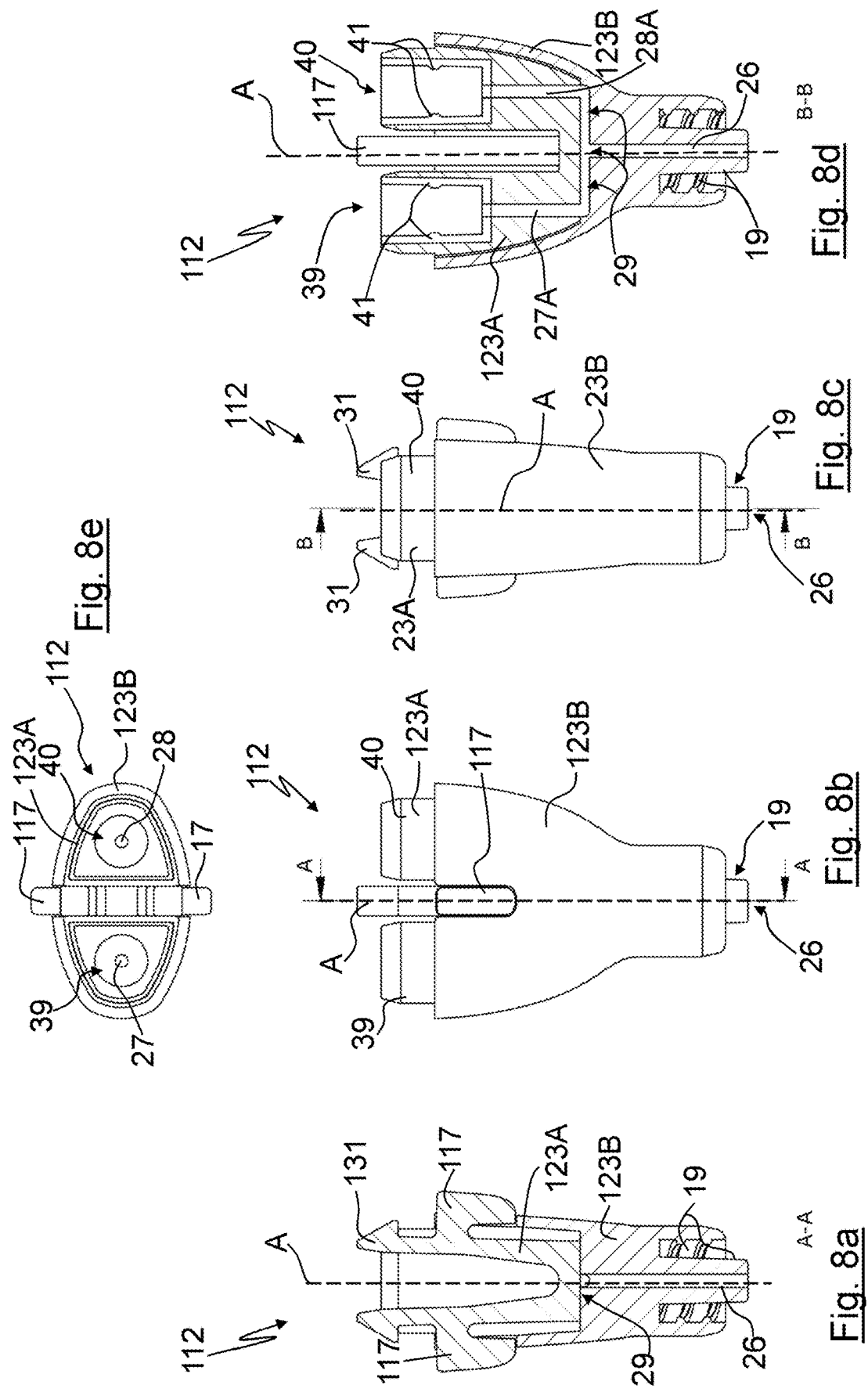

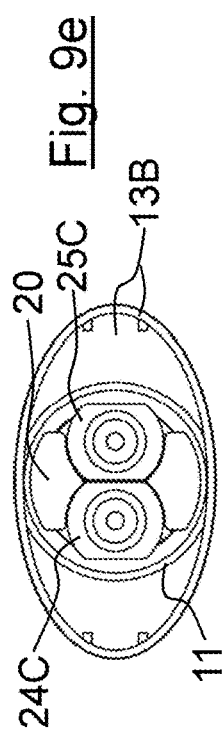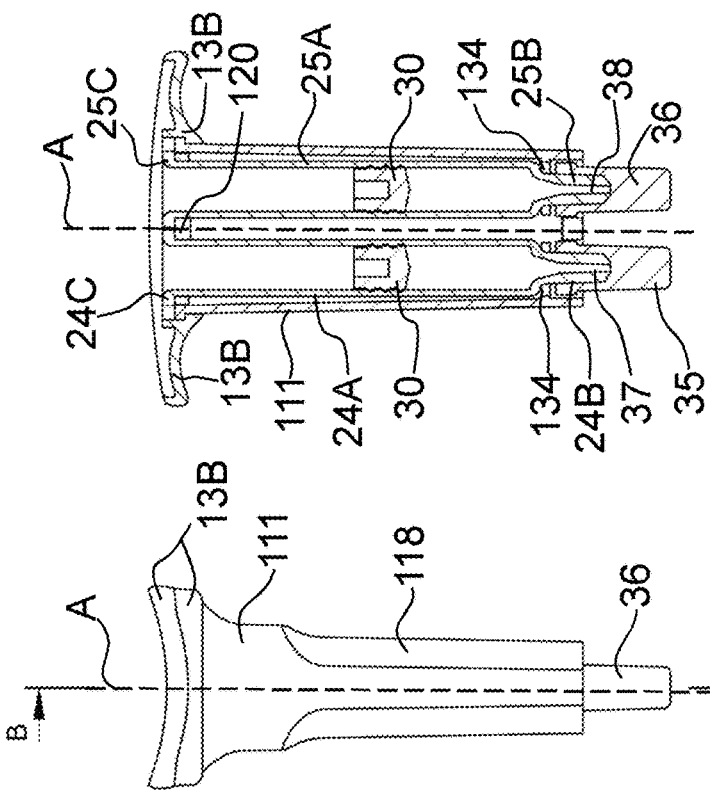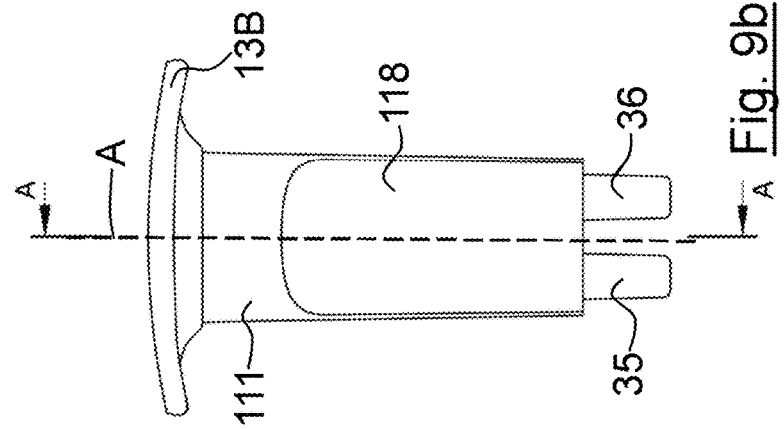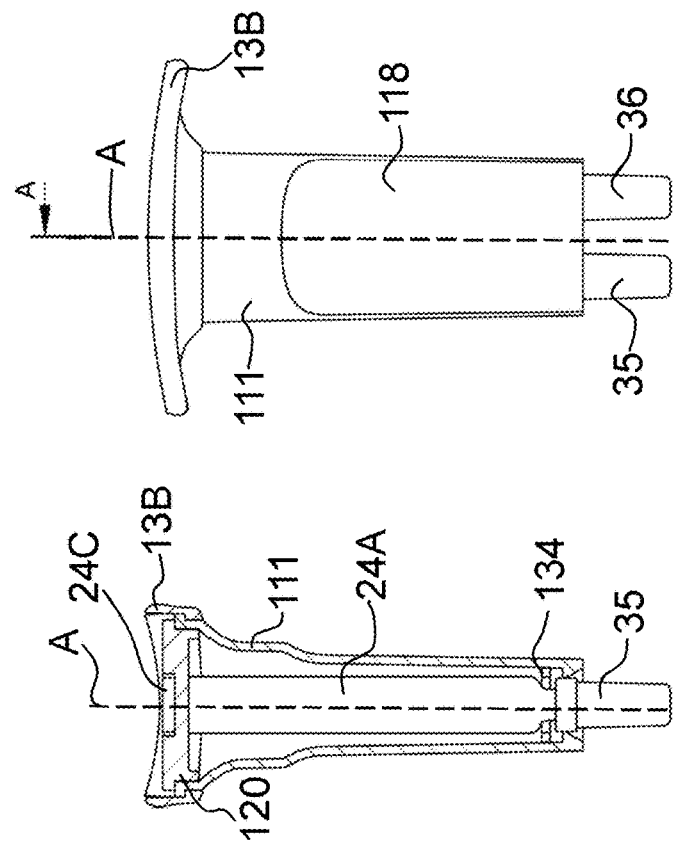

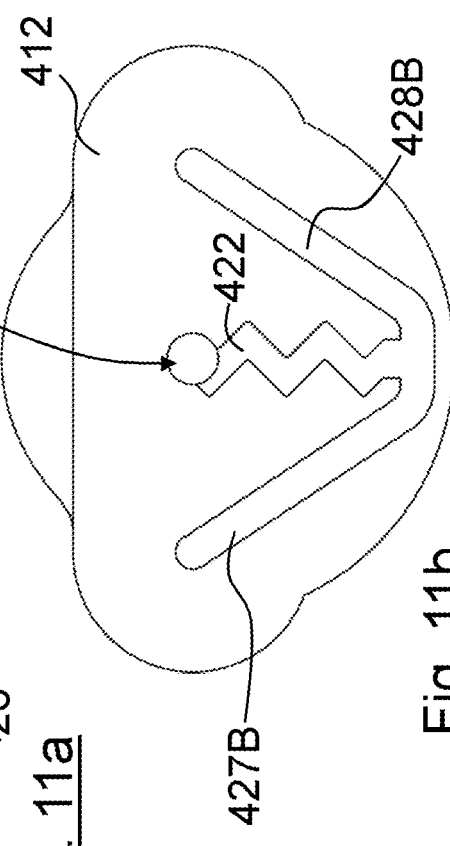
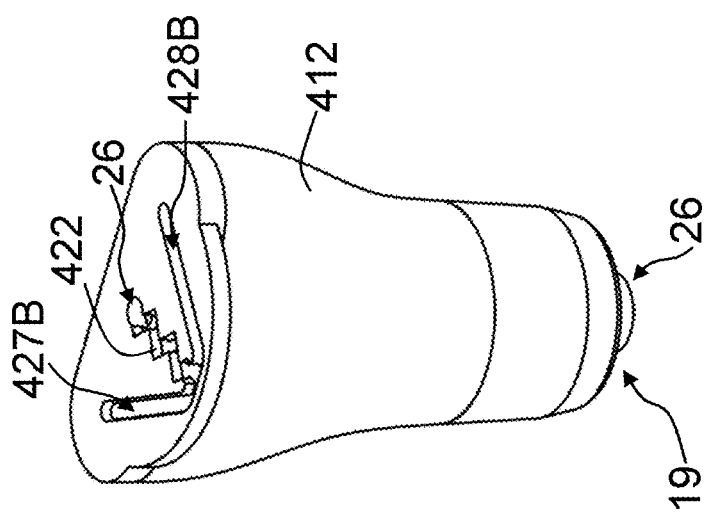
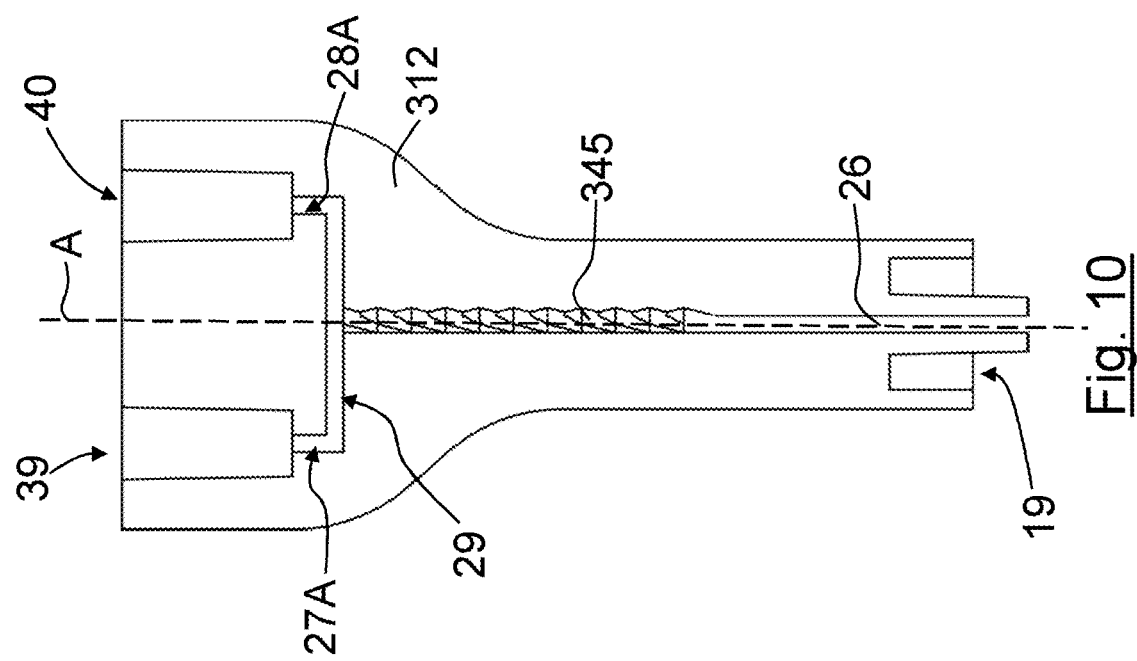
Fig. 11a
Fig. 11b
Fig. 10

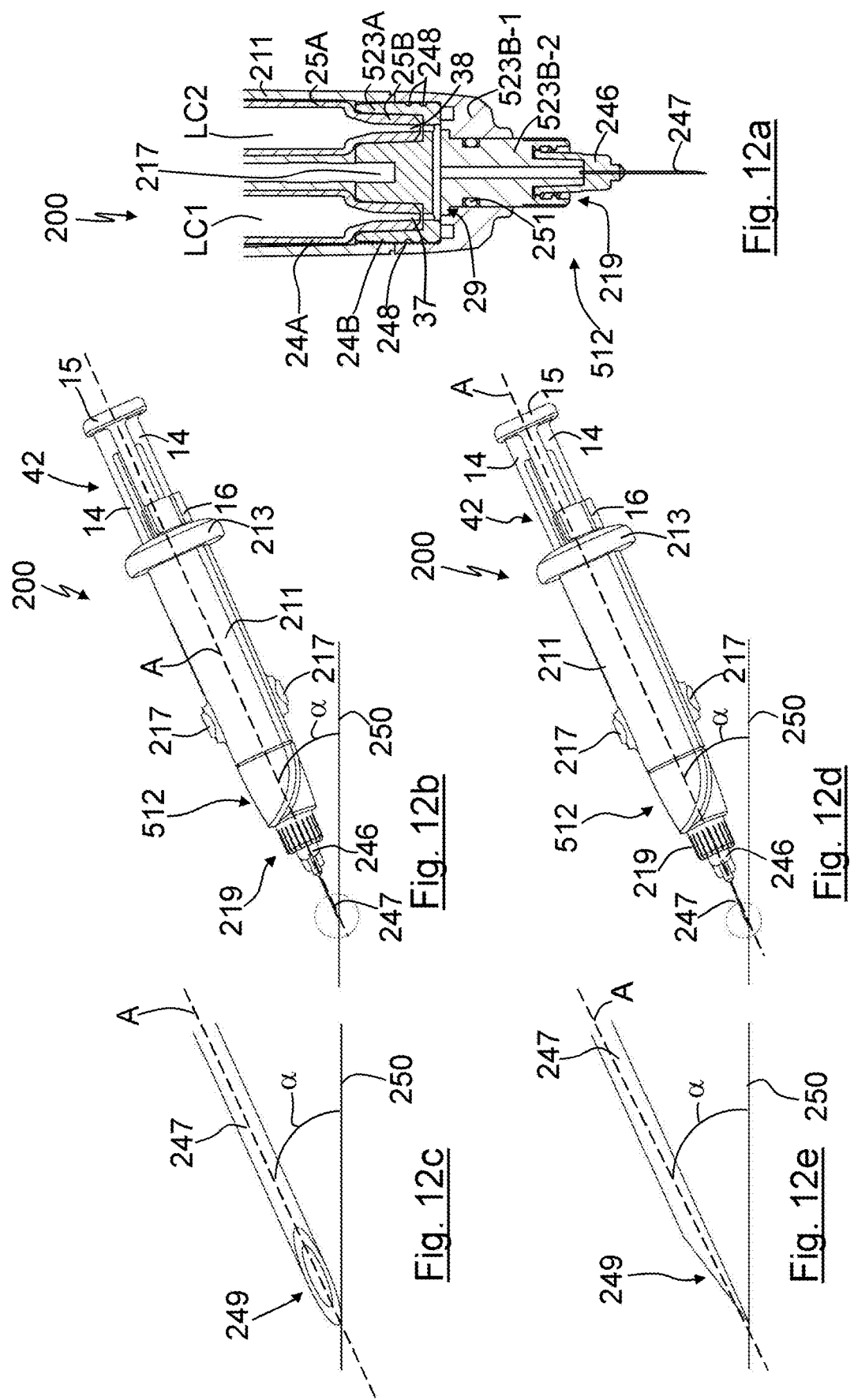

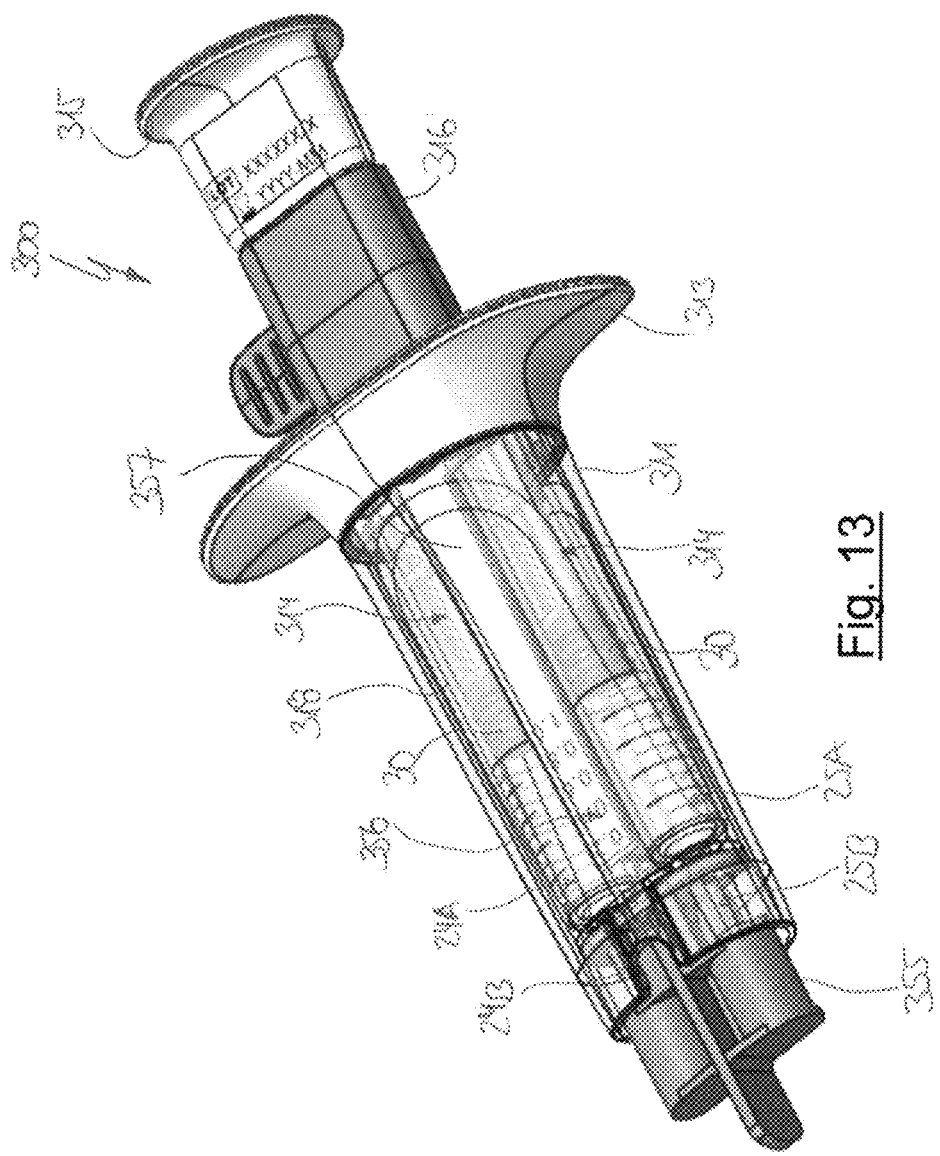
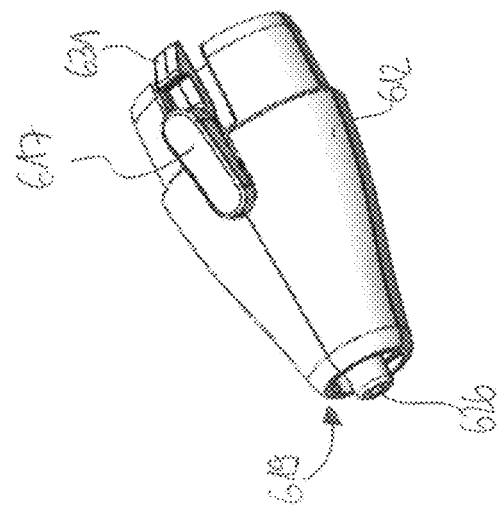
Fig. 13

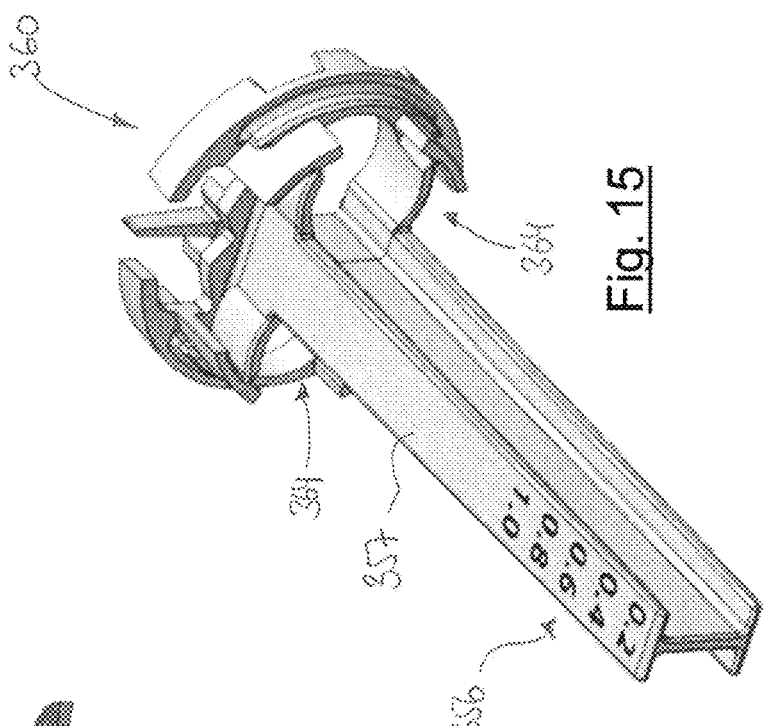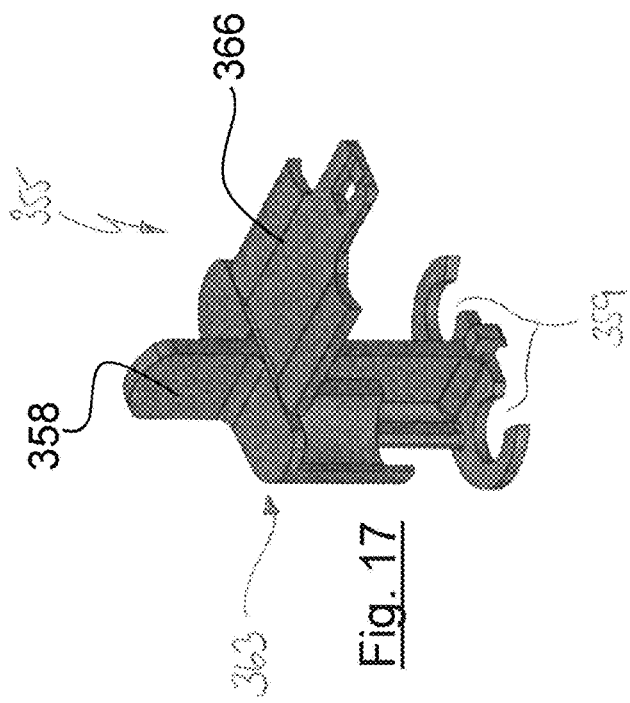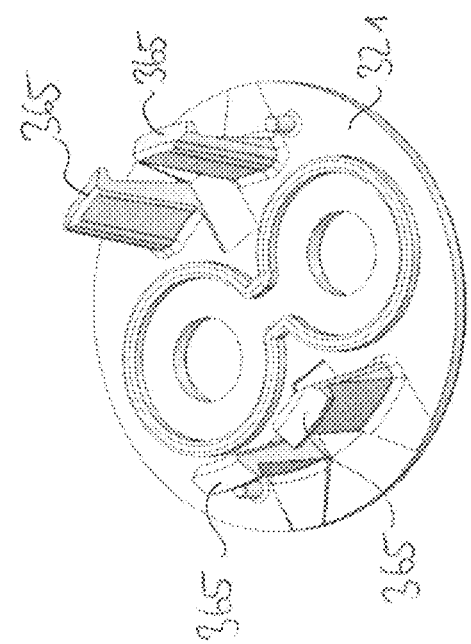

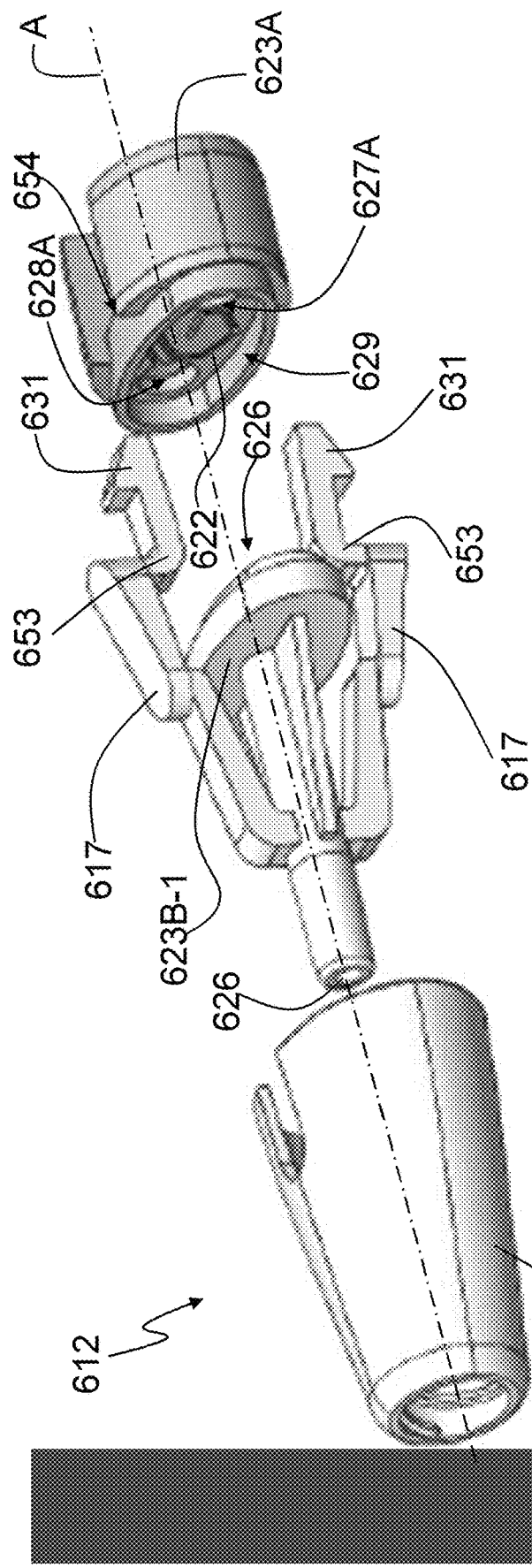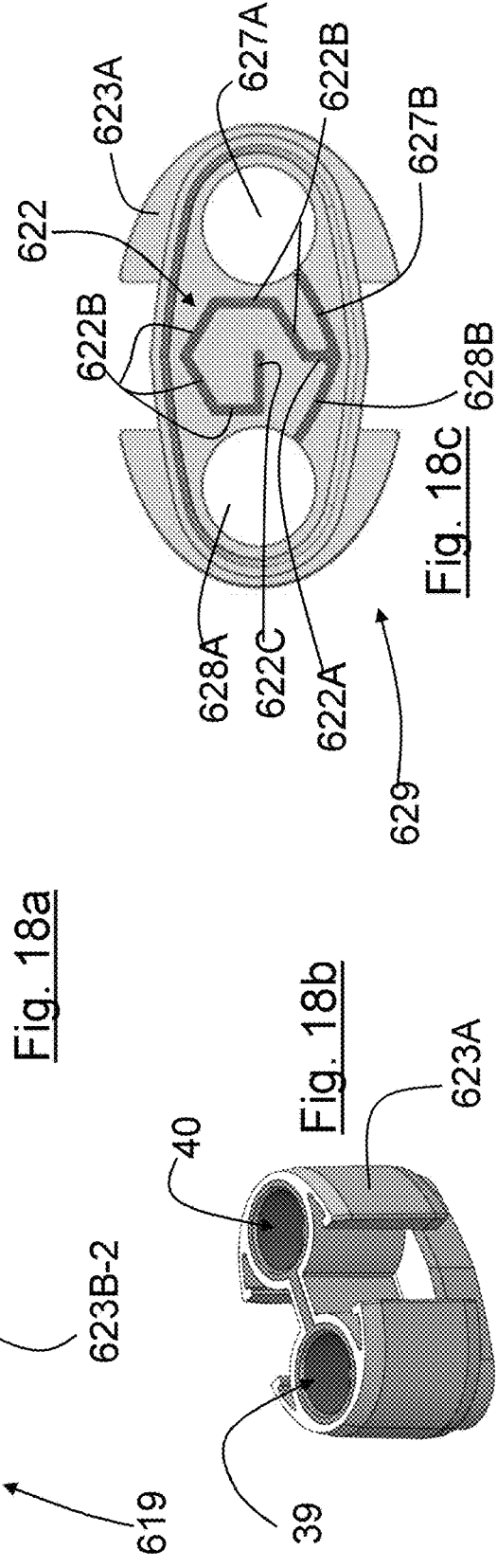
Fig. 18a
Fig. 18b
Fig. 18c

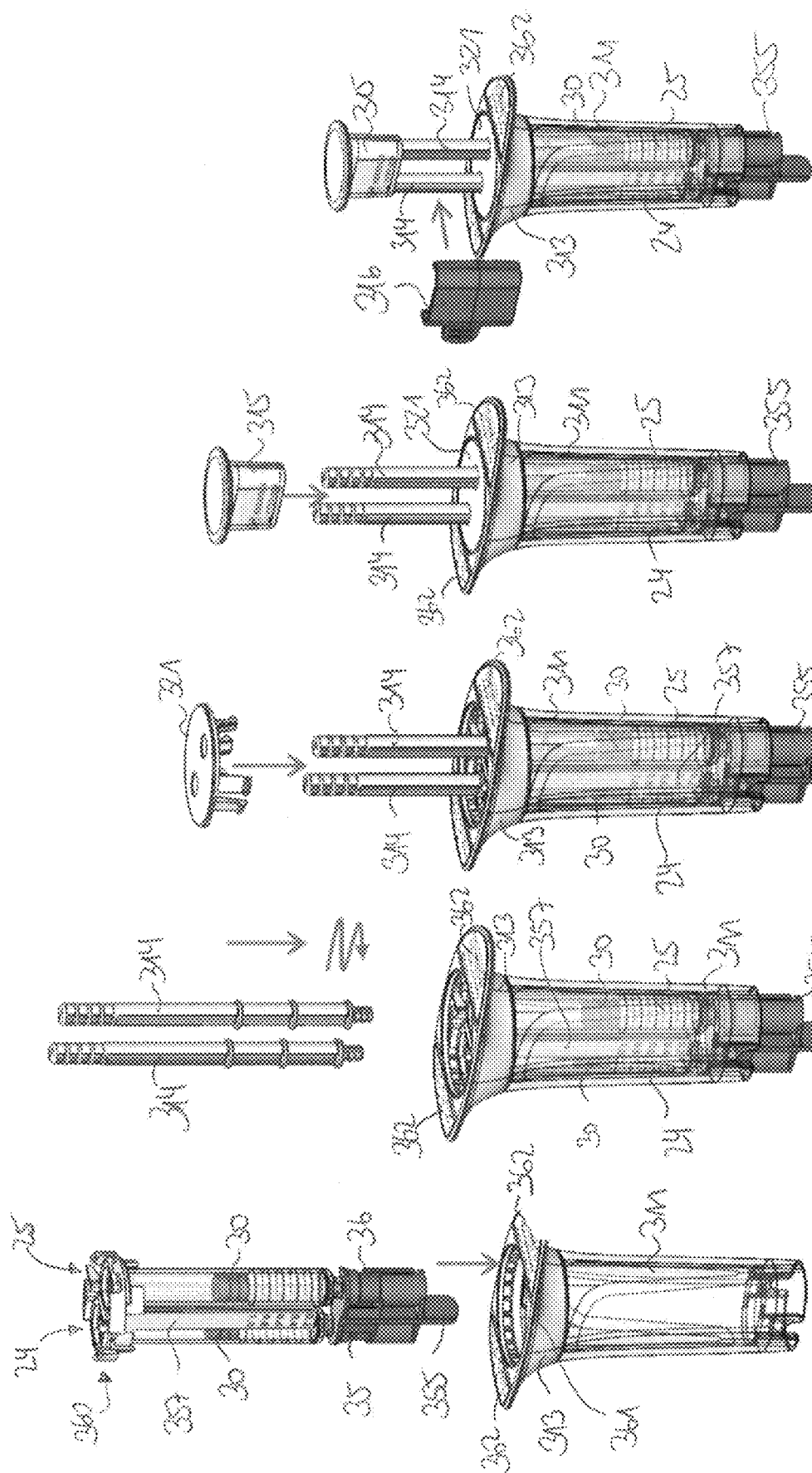

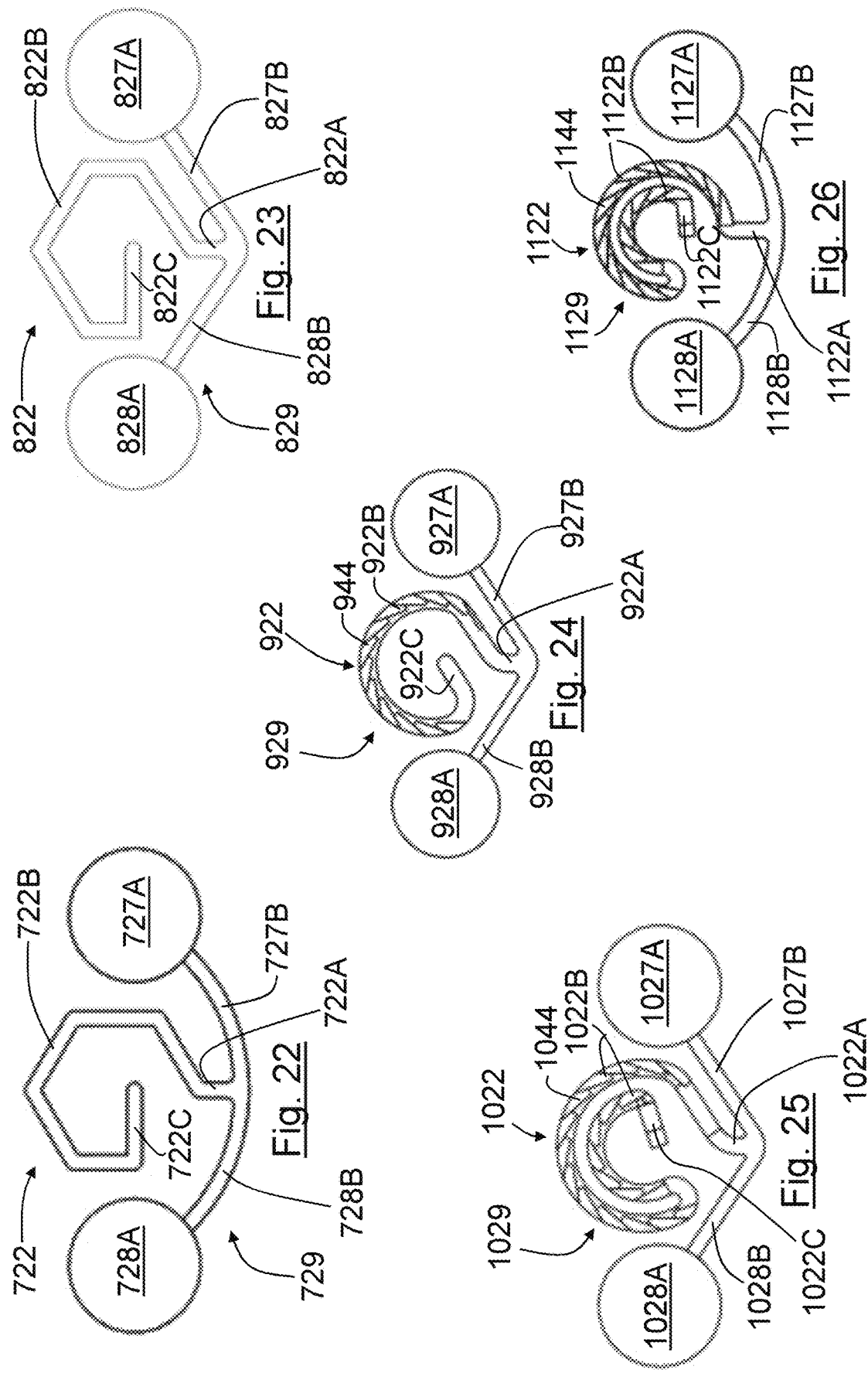

MIXING NOZZLE, APPLICATION DEVICE, KIT AND METHOD USING THE MIXING NOZZLE OR APPLICATION DEVICE

CROSS-REFERENCE TO RELATED APPLICATIONS

This application is the National Stage entry of International Application No. PCT/EP2018/065642, filed 13 Jun. 2018, which claims priority to European Patent Application No. 17175858.4, filed 13 Jun. 2017 and European Patent Application No. 17209718.0, filed 21 Dec. 2017.

BACKGROUND

Field

The present invention generally relates to a mixing nozzle for mixing at least two liquid compositions, such as a first liquid composition and a second liquid composition. The mixing nozzle is configured to be coupled to a body of a multi-component application device, in particular to a body of a two-component syringe assembly, for injection of a liquid composition, which body is configured to separately store said at least two solutions. The present invention further relates to a multi-component application device comprising said mixing nozzle and to a kit comprising said mixing nozzle or said application device. Furthermore, the present invention relates to a method using said application device or said kit, for example for replacing or filling a biological tissue or increasing the volume of a biological tissue.

DESCRIPTION OF RELATED ART

Summary

Mixing nozzles and multi-component application devices comprising mixing nozzles are known in the prior art for a broad range of applications. For example, US 2005/0243647 A1 discloses a mixing system and methods for mixing a plurality of constituents from a plurality of containers, wherein said mixing system includes a collar, a head, a cartridge, and optionally a base. If present, the base is configured to hold and secure at least two containers. The collar is configured for coupling to the containers. A head is coupled to the collar and contains the cartridge. The cartridge includes a plenum as mixing cavity, a mixing canal and an outlet, connected such that the materials are mixed as they pass through the plenum, the mixing canal and the outlet. The mixing canal includes a plurality of columns as flow impact elements, which may be of any shape, to facilitate mixing. The system can also include a leaver for activating release of the constituents from the containers.

DE 20 2006 004 738 U1 discloses a device for mixing two fluids, particularly for mixing two adhesive components of a two-component-adhesive, wherein the device comprises a body, an adapter element and a static mixing device with a static mixing element, wherein the adapter element is mounted exchangeable to the body and the static mixing device is mounted exchangeable to the adapter element.

WO 2008/009143 A1 discloses a dispensing device for a multiple cartridge or syringe, comprising a housing for receiving the cartridge with an internal thread and a rotatable portion that has a complementary thread, the two parts cooperating in such a manner that, by mutual rotation thereof, the rotatable portion is continuously displaceable relatively to the housing in the dispensing direction. The housing is configured to receive a cartridge that has two adjacent storage containers, and the thrust force of the rotatable portion is transmitted to a multiple ram without any pressure relief. This arrangement allows dispensing even highly viscous materials.

EP 0 800 361 B1 discloses a device for applying one or several fluids, particularly a multi-component fluid which is, for example, a tissue adhesive or a dental adhesive. The device is provided with a head piece comprising channels for each fluid, which extend from an inlet side of the head piece to a connection side of the head piece, and a tubular body comprising an inlet end facing the connection side of the head piece and an outlet end facing away from the inlet end. For mixing the several components, the head piece is Y-shaped and comprises two inlet channels running into a mixing channel. The two components to be mixed are contained in syringes, the barrels of the syringes being held together by a rack structure. Plunger rods of the syringes are coupled together by a bridging member such that both plunger rods are operated simultaneously so that the components to be mixed enter the Y-shaped head piece with the mixing channel at the same time.

U.S. Pat. No. 7,883,501 B2 discloses a double syringe delivery system for fibrin glue or dentistry holding a pair of syringes in a manner so as to accommodate the simultaneous activation of the plunger of each syringe in order to effect simultaneously delivery of the contents of each syringe. The double syringe delivery system includes a delivery mechanism for delivering the contents of both syringes to a site of application. It further includes an elongated support member that is positioned between the two syringe bodies. The elongated support member has resilient, C-shaped clamps on one end of the support member. The clamps are designed to be removable clamped onto the applicator so that the syringe barrels will be held together in a parallel manner. The elongated support member further comprises finger grips. A plunger connects the two syringe plungers to so that they can be simultaneously activated.

DE 10 2013 103 552 A1 discloses a double-chamber syringe for mixing and application of a two components dental material, wherein the device comprises a mixing nozzle with a pre-mixing zone and a main mixing zone. The mixing nozzle comprises several inlet channels extending linear and facing one another. In the main mixing zone, an impact element is arranged.

For many applications, in particular medical or cosmetic applications, it is important to observe the required mixing ratio exactly and to achieve a homogenous mixing. Also, it is generally desirable to avoid dead zones in the mixing area to avoid clotting or unwanted interactions of the mixed material within the application device. Furthermore, precise application of discrete amounts of material is often critical and low application forces, e.g. low injection forces, are highly desirable in terms of precision of administration.

OBJECTS OF THE INVENTION

In view of the above, the object of the present invention is the provision of a mixing nozzle capable of mixing at least two liquid compositions, e.g., at least a first liquid composition and a second liquid composition, with high precision to homogeneity and, when being coupled to a body of a multi-component application device, providing ease of application of liquid compositions.

SUMMARY OF THE INVENTION

The present invention provides a mixing nozzle, a multi-component-application device comprising said mixing nozzle, a kit comprising said mixing nozzle or said application device, and a method using said application device or said kit as defined in the appended claims.

The mixing nozzle of the present invention offers the benefit of improved mixing, both in terms of mixing precision and homogeneity, of at least two liquid compositions. Furthermore, the mixing nozzle of the present invention is advantageous in that it, when coupled to a body of a two- or multi-component application device, provides an improved ease of application, in particular a facilitated and more convenient injection of liquid compositions such as hydrogels, emulsions, dispersions, solutions and so forth. Moreover, the mixing nozzle of the present invention allows for a reduced risk of clotting and/or undesirable reaction of the materials in the mixing nozzle.

In a first aspect, the present invention provides a mixing nozzle for mixing at least a first liquid composition and a second liquid composition, the mixing nozzle being configured to be coupled to a body of a multi-component application device, in particular to a body of a two-component syringe assembly, for injection (e.g., intradermal and/or subcutaneous injection) of a liquid composition, for example a hydrogel (e.g. a soft tissue filler in the form of a hydrogel), optionally comprising further components such as neurotoxins and cells and said body being configured to separately store said at least first and second liquid compositions.

The mixing nozzle comprises at least two fluid inlet channels for receiving the separately stored liquid compositions to be mixed, a mixing zone having at least one mixing channel for mixing the liquid compositions while they flow through the mixing channel, and an outlet channel connectable to an injection needle having a lumen extending along a first longitudinal axis. Said outlet channel of the mixing nozzle is fluidly connected or connectable with said inlet channels of the mixing nozzle by said mixing zone.

The mixing zone, in particular at least said mixing channel, is configured to change flow direction of a mixing flow from a first flow direction at least to a second flow direction, wherein said mixing zone, in particular at least said mixing channel, is configured to change flow direction of a mixing flow from a first flow direction at least to a second flow direction, wherein said mixing channel comprises flow manipulation elements arranged alternating within the mixing channel for changing flow direction and/or extends at least partly or entirely alternating at least in a first direction and a second direction, and/or extends at least partly along an n-cornered contour, in particular along a hexagonal or an octagonal contour, and/or extends at least partly along a star-shaped contour.

Furthermore, the mixing nozzle according to the present invention, at least said mixing channel comprises at least one segment extending at least partly in radial direction to or at least partly arc-shaped around said first longitudinal axis, particularly at least partly in a plane perpendicular to said first longitudinal axis.

In general, the mixing nozzle comprises connection means for connecting the mixing nozzle to an injection needle. The connection means of the mixing nozzle may be rotatable around said first longitudinal axis to adjust needle orientation relatively to the mixing nozzle and/or the application device.

The mixing nozzle may further be assembled of at least a first part and a second part, wherein a joint between said first part and said second part passes at least partly through the mixing nozzle adjacent to said mixing channel and/or at least partly within said mixing channel.

In a second aspect, the present invention provides a multi-component application device, particularly a two-component syringe assembly, for discharging a mixed composition of at least a first liquid composition and a second liquid composition and for injection of the mixed composition. The multi-component application device comprises a mixing nozzle according to the present invention and is configured to separately store the liquid compositions to be mixed, i.e. the at least first and second liquid compositions.

The multi-component application device according to the present invention typically comprises a body, a plunger assembly and a handle, wherein the handle may be, and preferably is, rotatable around said first longitudinal axis to adjust handle orientation relatively to said mixing nozzle and/or said body. Furthermore, said mixing nozzle is preferably detachable mounted to said body, particularly by at least one snap-fit connection.

In a third aspect, the present invention provides a kit, comprising a mixing nozzle according to the present invention or an application device according to the present invention.

In a fourth aspect, the present invention relates to a method for cosmetic or therapeutic treatment or application, particularly for replacing or filling a biological tissue or increasing the volume of a biological tissue, wherein an effective amount of an injectable liquid composition, particularly an injectable dermal filler composition, is to be administered or is administered to a subject by using an application device according to the present invention and/or a kit according to the present invention.

Preferred embodiments of the present invention are set forth in the appended claims. Further embodiments and other objects, advantages and features of the present invention will become apparent from the following detailed description of the invention, the illustration of particular embodiments and the accompanying figures.

DETAILED DESCRIPTION OF THE INVENTION

In a first aspect, the present invention relates to a mixing nozzle for mixing at least a first liquid composition and a second liquid composition, the mixing nozzle being configured to be coupled to a body of a multi-component application device, in particular to a body of a two-component syringe assembly, for injection of a liquid composition. Said body is configured to separately store said at least first and second liquid compositions.

The mixing nozzle comprises at least two fluid inlet channels for receiving the separately stored liquid compositions to be mixed, a mixing zone having at least one mixing channel for mixing the liquid compositions while they flow through the mixing channel, and an outlet channel connectable to an injection needle having a lumen extending along a first longitudinal axis, wherein said outlet channel of the mixing nozzle is fluidly connected with said inlet channels of the mixing nozzle by said mixing zone.

The mixing zone, in particular at least said mixing channel, is configured to change flow direction of a mixing flow from a first flow direction at least to a second flow direction wherein said mixing zone, in particular at least said mixing channel, is configured to change flow direction of a mixing flow from a first flow direction at least to a second flow direction, wherein said mixing channel comprises flow manipulation elements arranged alternating within the mixing channel for changing flow direction and/or extends at least partly or entirely alternating at least in a first direction and a second direction, and/or extends at least partly along an n-cornered contour, in particular along a hexagonal or an octagonal contour, and/or extends at least partly along a star-shaped contour.

The mixing channel preferably extends at least partly or entirely in a plane perpendicular to said first longitudinal axis. However, the mixing channel may also, i.e. additional or alternatively, extend at least partly or entirely in a plane parallel to the first longitudinal axis or different from that.

Preferably, the mixing channel may extend at least partly alternating between at least a first flow direction and a second flow direction. In an embodiment, in order to extend at least partly alternating between at least a first flow direction and a second flow direction, said mixing channel may extend at least partly or entirely zig-zag-shaped and/or meander-shaped, preferably in a plane perpendicular to the first longitudinal axis. Furthermore, the mixing channel may at least in one segment or section be designed as a "chaotic serpentine", i.e. having an erratic, serpentine-shaped pathway.

In a particular embodiment for extending at least partly along an n-cornered contour, in particular along a hexagonal or an octagonal contour, said mixing channel may extend over a length of at least 50% of said contour related to being closed in circumferential direction, wherein preferably said mixing channel may extend over a length of at least 75% of said contour. In a preferred embodiment of a mixing nozzle according to the present invention, said mixing channel extends at least over n/2 edges of said n-cornered contour, in particular over at least (n/2+1) edges up to more than (n−1) edges, in particular over 4, 5, or 6 edges of a hexagon contour, in particular over at least 5, 6, 7 or 8 edges of an octagonal contour. Preferably, a length of the edges of the n-cornered contour is equal. In an alternative embodiment, the edges of the n-cornered contour may have different lengths.

In a particular embodiment for extending at least partly along a star-shaped contour, said mixing channel may extend along the contour of an at least 5-pointed star, preferably along the contour of a at least 6-pointed star, particularly along the contour of an at least 8-pointed star.

In order to achieve sufficient mixing of the components, a minimum length of the flow pathway being flowed through by the combined liquid compositions is required, particularly a minimum length of the mixing channel. However, the length of the nozzle in direction of the first longitudinal axis, i.e. in injection needle direction, is limited because of ergonomic reasons. For precise injections (e.g. intradermal and/or subcutaneous injections) and convenient application of discrete amounts of a liquid composition, e.g. a hydrogel, in particular a dermal filler composition in the form of a hydrogel, to a target site of a human body with desirable injection angles of minimum 5 degrees up to 15 degrees, in particular with injection angels of 8 degrees up to 10 degrees, the distance in longitudinal direction from a syringe handle or a syringe finger grip to a tip of the injection needle connected to the application device should be as short as possible. Consequently, the extension of the mixing zone in direction parallel to the first longitudinal axis should be as short as possible. On the other hand, it should be as long as necessary to achieve sufficient mixing results.

With a mixing nozzle according to the present invention, a sufficient mixing of the components can be achieved with a short extension respectively length of the mixing nozzle in the first longitudinal direction, in particular without one or more long static mixing elements extending along the first longitudinal axis. Therefore, a mixing nozzle according to the present invention provides enhanced ease of use, in particular facilitated and more convenient injection. Furthermore, with a mixing nozzle according to the present invention an application device for very precise injections, in particular intradermal or subcutaneous injections of a liquid composition, can be provided. Generally, the more flow direction changes are realised, the better the achievable mixing of the components.

As used herein, the term "nozzle" refers to a device, which can be arranged as a tip on a proximal end of an application device, e.g. as a tip on a proximal end of a syringe and/or or a syringe assembly and/or a similar application device. A "mixing nozzle" is a nozzle, which is formed to mix and/or combine at least two fluids to a mixed fluid, wherein a "mixing nozzle" in the context of the present invention preferably comprises at least one outlet for discharging the mixed fluid out of the mixing nozzle.

The term "application device", as used herein, refers to an application device being configured for discharging at least one component stored in that device. Further, the term "application device", as used herein, is intended to encompass multi-component, including two-component, application devices, in particular a multi- or two-component syringe assembly.

The term "body", as used herein, refers to a part of an application device, wherein the body serves as a holder and/or carrier being configured for receiving and/or holding at least one primary packaging container, e.g. a container, a cartridge, a carpule, an ampoule, a vial, a pouch or a syringe, in particular a mono-chamber syringe or a double-chamber syringe, preferably for receiving and/or holding of at least one primary packaging container filled with one of the liquid compositions, or wherein the body is configured to store the at least first and second liquid compositions, wherein for this purpose the body preferably comprises at least a first chamber and a second chamber, separated from each other.

The term "syringe", as used herein, refers to a device operating as a manually operating reciprocating pump, usually comprising a plunger and/or a piston that fits tightly within a usually cylindrical tube or chamber or container or barrel, wherein the plunger can be pulled and pushed along the inside of the tube along a longitudinal axis of the tube, allowing to take in and expel a fluid through a discharge orifice at a proximal end of the tube.

The term "syringe assembly", as used herein, refers to a syringe or a syringe-like application device being configured for discharging at least one component stored in that device.

The term "chamber", as used herein, refers to a storage volume or storage cavity being part of the body of the application device, i.e. to a volume or cavity manufactured integrally with the body or inserted unexchangeable, wherein the terms "container" and "barrel", which are used interchangeably herein, refer to separate storage volumes, i.e. to separate volumes (cavities) not integrally manufactured with the body, which can be inserted and/or fixed to the body and which are preferably exchangeable generally, however may be not by the user. The term "container", as used herein, is not particularly limited and includes, for example, glass or plastic bottles, vials, carpules, ampoules, cartridges or any other sealed container.

The term "multi-component application device", as used herein, refers to an application device being configured for discharging at least two components, e.g. liquid compositions, stored separately in that device, wherein a "multi-component application device" according to the invention preferably comprises a plunger and/or a piston that fits tightly within a usually cylindrical tube or chamber or container for each component. The term "store separately", as used herein, means "store separated from another, preferably in different barrels" to exclude mixing during storage.

Within the context of the present invention, the term "injection" may refer to intra-, inter- or subdermal injection or subcutaneous injection. The term "intradermal injection", as used herein, refers to an injection method, where a composition is administered into the epidermis by injection. The term "subcutaneous injection", as used herein, refers to an injection method, where a composition is administered into the hypodermis by injection, i.e. into the subcutis or a subcutaneous tissue. The term "needle", as used herein, is intended to comprise or be synonymous to a "cannula" or any other needle-like objects suitable for injection.

As used herein, the term "soft tissue filler" broadly refers to a material designed to add volume to areas of soft tissue deficiency. A "dermal filler" or "dermal filler composition", as used herein, is generally a substance that adds, replaces or augments volume under the skin leading to, e.g., smoothened skin wrinkles, augmented lips, improved skin appearance, or treated scars. A dermal filler composition of the present invention is, like a soft tissue filler, generally "injectable". Further, a dermal filler is generally used in the dermis area, such as below the epidermis or above the hypodermis and as such may be injected subcutaneously or intradermally, or some combinations.

The term "composition", as used herein, is not particularly limited and may be, e.g., a liquid composition. Preferably, the composition may be a composition that is used or suitable for use as a soft tissue filler, in particular a dermal filler. According to the present invention, a "dermal filler" or a "dermal filler composition" may be an in situ crosslinkable composition made by combining and/or mixing a first liquid composition (e.g., a first precursor solution) with a second liquid composition (e.g., a second precursor composition). The first and second liquid compositions are preferably sterilized by subjecting the first liquid composition and the second liquid composition to moist heat, e.g. to autoclaving, preferably after filling the first and second liquid compositions into an application device.

The term "liquid composition", as used herein, should be understood to encompass a liquid (e.g., an aqueous liquid), a solution (e.g., an aqueous solution), a suspension (e.g., an aqueous suspension), a dispersion (e.g., an aqueous dispersion), an emulsion (e.g., an aqueous emulsion), a gel (e.g., a hydrogel) etc., and mixtures thereof.

Preferably, the first liquid composition and the second liquid composition according to the present invention are, independently from each other, a liquid solution, particularly an aqueous solution, or a gel, particularly a hydrogel. In particular, the liquid compositions may also be precursor solutions, more particularly aqueous precursor solutions, capable of in situ forming a crosslinked gel. This is, the concurrent mixing and injection of the precursor solutions results in the in situ formation of a crosslinked gel at the target site in the human body.

The term "gel", as used herein, generally refers to a material having fluidity at room or body temperature between that of a liquid and solid. The term "gel" encompasses "hydrogel" which, as used herein, is intended to mean a hydrated material or a material capable of absorbing water.

The term "inlet channel", as used herein, refers to a channel defining a flow path with at least one inlet opening, preferably only one inlet opening, being configured for receiving at least one of the separately stored liquid compositions, wherein preferably an inlet channel, as used herein, is flowed through by only one of the liquid compositions.

The term "mixing zone", as used herein, refers to a zone defining one or more common flow paths or common flow zones for being flowed through by at least the first liquid composition and the second liquid composition. Preferably, in the "mixing zone" combining and/or mixing of at least the first liquid composition with the second liquid composition occurs. As used herein, the term "alternating" means changing flow direction at least from a first flow direction to a second flow direction and again to the first flow direction (1-2-1). In particular, "alternating" as used herein means periodically changing, e.g. 1-2-1-2 or 1-2-3-1-2-3 or 1-2-3-2-1-2-3.

The term "mixing channel", as used herein, refers to a channel defining a common flow path for at least the first liquid composition and the second liquid composition, wherein a "mixing channel" does not need flow manipulating elements necessarily, but may have one or more of them.

The term "outlet channel", as used herein, refers to a channel defining a flow path with at least one outlet opening, preferably only one outlet opening, being configured for discharging the liquid composition made by combining and/or mixing the first liquid composition with the second liquid composition out of the mixing nozzle, wherein in the outlet channel further combining and mixing can occur, i.e. an outlet channel can also be, at least partly or entirely, a mixing channel.

As used herein, the term "injection needle" refers to a needle for injection, preferably to a hypodermic injection needle. An injection needle according to the inventions described herein can have one of an amount of different tips, particularly one tip having a cut of an amount of different cuts, i.e. different bevelled edges, e.g. the tip of an injection needle according to one of the inventions described can have a in the state of the art so called "standard bevel", a "short bevel" or a "true short bevel".

The term "segment", as used herein, in the context of a channel refers to a passage or a section of the channel, i.e. to a part of the channel along its length. Preferably, each fluid inlet channel of the mixing nozzle is configured to be fluid connected to an outlet channel of a chamber or a container or a barrel of a multi-component application device, wherein particularly each chamber or container or barrel is fillable or pre-filled with one of the liquid compositions to be mixed.

The term "fluid connected", as used herein, refers to a leak-proof connection which can be flowed through by a fluid.

In an embodiment of the mixing nozzle according to the present invention, at least one of said at least two fluid inlet channels has at least one segment extending at least partly arc-shaped around said first longitudinal axis. Preferably, said at least one segment of the inlet channel extends in a plane perpendicular to said first longitudinal axis.

Using arc-shaped inlet channels, the multiple components to be mixed can be combined in an advantageous manner regarding the mixing result. The improved mixing result is attributable to the fact that by the arc-shaped inlet channels in the abutting mixing zone, particularly in the abutting mixing channel, the turbulent flow accountable for the mixing of the at least two liquid compositions can be improved. Particularly, in the turbulent flow a swirl can be generated, resulting in an improved mixing of the liquid compositions compared to entirely linear inlet channels.

As used herein, the term "arc-shaped" refers to a non-linear extending pathway, in particular to an at least partly curved pathway. This is, at least one of said inlet channels of a mixing nozzle according to the first invention has at least one segment extending at least non-linear, in particular at least partly curved, around said first longitudinal axis. Preferably additional and/or alternative to the extension in a plane perpendicular to said first longitudinal axis, at least one of said arc-shaped segments of at least one of said inlet channels at least partly extends arc-shaped along an inner lateral surface of a cone, in particular arc-shaped along an inner lateral surface of a rotationally symmetric cone, preferably of a cone with its cone tip on said first longitudinal axis. This can be an advantage in some use cases, in particular regarding package and/or flow behaviour.

Preferably, at least one of said arc-shaped segments of at least one of said inlet channels extends at least partly or entirely circle-arc-shaped, particularly circle-arc-shaped around said first longitudinal axis. With a at least partly circle-arc-shaped inlet channel in some use cases flow homogeneity can be improved, in particular an extra homogeneous flow, particularly a more laminar flow can be achieved.

The term "homogeneous", as used herein, means uniformly mixed, dispersed or diluted throughout the mixture, dispersion or solution, or refers to a material of uniform structure and/or composition throughout.

Preferably, at least two of said arc-shaped segments of at least two different inlet channels merge into each other, particularly tangential in circumferential direction, preferably with their outlets, particularly at or near the inlet of the mixing zone, preferably at or near the inlet of at least one mixing channel. Herewith, in particular with tangential merging and simultaneous transition into the mixing zone, beneficial effects regarding mixing results can be achieved in a lot of use cases.

Preferably, at least one of said arc-shaped segments of at least one of said inlet channels, particularly of at least two inlet channels, extends arc-shaped about a circumferential angle of at least 30, 60 or 90 degrees up to an angle of maximum 90, 120 or 150 degrees, particularly with a circumferential angle of 90 degrees. Herewith, in particular with a circumferential of 90 degrees, in a very easy manner two inlet channels can merge tangentially into each other, in particular with simultaneous transition into the mixing zone, with beneficial effects regarding mixing results in a lot of use cases.

Preferably, at least one of said inlet channels of the mixing nozzle, preferably each inlet channel, comprises at least a first segment and a second segment, wherein preferably the first segment of at least one of said inlet channels is arranged in flow direction ahead to the second segment of that inlet channel, wherein particularly at least one of the first segments extends from an inlet of the inlet channel on, and wherein preferably at least one of the second segments extends to an outlet of the inlet channel, i.e. the second segment preferably extends until the inlet of the mixing zone.

Preferably, at least one of the first segments of at least one of said inlet channels, particularly each first segment, extends at least partly or entirely parallel to said first longitudinal axis. Herewith, in a very easy manner, fluid connection means being configured for easy establishing of fluid connections between the chambers and/or containers and the mixing nozzle can be realized.

Preferably, at least one the first segments of at least one of the inlet channels, particularly all first segments of all inlet channels, is (are) at least partly or entirely surrounded by a female Luer-cone connector for establishing a Luer-cone connection with a male Luer connector of a chamber of the body or a container arranged in the body, preferably for establishing a Luer-cone connection with a male Luer connector of a container, in particular for establishing a Luer-cone connection with a male Luer connector of a usual mono-chamber syringe as known in prior art.

Preferably, at least one of the second segments of at least one of the inlet channels, preferably each second segment, extends at least partly or entirely arc-shaped around said first longitudinal axis, preferably in a plane perpendicular to said first longitudinal axis.

Preferably, at least one of said inlet channels comprises a first segment extending parallel to said first longitudinal axis and a second segment extending at least partly or entirely arc-shaped around said first longitudinal axis, preferably in a plane perpendicular to said first longitudinal axis. Herewith the beneficial effects of easy removal of the liquid compositions out of the chambers or containers can be combined with the improvement of mixing and/or package.

Preferably, said outlet channel of the mixing nozzle extends at least partly or entirely along said first longitudinal axis. Herewith, in a very easy manner, a fluid connection between the outlet channel and the lumen of an injection needle can be established for dispensing the mixed liquid compositions from the mixing nozzle into the injection needle and onwards for injection into a tissue of a target.

Preferably, the mixing nozzle is designed for mixing at least the first and second liquid compositions with a mixing ratio of 1:1. However, by changing volume and cavity geometry of the mixing zone, in particular of at least one of said mixing channels, the mixing ratio can easily be adapted and/or adjusted to another required mixing ratio.

Preferably, the mixing nozzle is designed to mix first and second liquid compositions typically having a low dynamic viscosity of 0.001 Pa·s to 5.0 Pa·s, in particular 0.005 Pa·s to 3.0 Pa·s, preferably 0.001 Pa·s to 1.0 Pa·s, more preferably 0.001 Pa·s to 0.1 Pa·s, as determined by oscillatory rheological measurements at 1 Hz and 25° C. Furthermore, the first and second liquid compositions may both be characterized by a low extrusion force of from 0.01 N to 15 N, preferably 0.1 N to 10 N, more preferably 0.5 N to 7.5 N, and most preferably 0.01 N to 50 N or 1.0 N to 5.0 N, as measured through a 30 G needle (TSK Laboratory) at an extrusion rate of about 0.21 mm/sec using a standard 1.0 ml glass syringe (BD Hypak SCF, 1 ml long RF-PRTC, ISO 11040, inner diameter of 6.35 mm).

The mixing nozzle is, for example, suitable for dispensing a liquid in situ cross-linkable composition having a complex viscosity of 0.1 Pa·s to 100 Pa·s or 0.1 Pa·s to 75 Pa·s or 1.0 Pa·s to 75 Pa·s, more preferably from 1 Pa·s to 50 Pa·s or from 5 Pa·s to 50 Pa·s, when measured as described above. Furthermore, the injection force of the composition is preferably 0.01 N to 20 N or 0.01 to 10 N, more preferably 0.1 N to 10 N, and most preferably 1.0 N to 5.0 N, when measured as described above.

In particular, the mixing nozzle may be designed to mix a first liquid composition A and a second liquid composition B, the first and second liquid compositions being capable of in situ forming a crosslinkable dermal filler composition. The first liquid composition A is preferably a solution of a polysaccharide derivative functionalized with a first reactive group, in particular a nucleophilic group, and the second liquid composition B is preferably a solution of a polysaccharide derivative functionalized with a second reactive group, in particular an electrophilic group. The nucleophilic group and the electrophilic group form a covalent linkage in situ following co-injection of the first and second polysaccharide derivatives to a target site in the human body, resulting in the in situ formation of a cross-linked hydrogel at the target site. Particularly preferred, the first liquid composition is a solution of a first hyaluronic acid (HA) derivative functionalized with said first reactive group, in particular a solution of a hydrazide functionalized first hyaluronic acid (HA) derivative, and the second liquid composition B is a solution of a second hyaluronic acid (HA) derivative functionalized with said second reactive group, in particular a solution of an aldehyde functionalized second hyaluronic acid (HA) derivative.

Preferably, the mixing nozzle comprises or is made of thermoplastic synthetic material, particularly of biocompatible and/or sterilisable material, which is preferably inert towards the liquid compositions as e.g. so called "medical grade" material. In particular, the mixing nozzle comprises one or more of the following materials: ABS (acrylic nitrile butadiene styrene), POM (polyoxymethylene), PC (polycarbonate), SAN (styrene acrylic nitrile), PP (polypropylene), silicon, TPE (thermoplastic elastomer) and/or rubber, or is made out of at least one of these materials. Furthermore, the mixing nozzle can comprise or can be made of plastic filled with particles as for, e.g., glass particles, metallic, in particular magnetic particles and/or conductive particles. Moreover, the mixing nozzle can comprise one or more structure elements as, e.g., grids or solid or hollow geometrical figures (cubes, tetraeders, prisma), which are preferably overmolded at least partly by the nozzle material and/or which are made by two-component injection molding and which particularly serve as flow manipulating elements.

In an embodiment of the mixing nozzle according to the present invention, at least one of said mixing channels comprises at least a first segment and a second segment, wherein at least one of the at least first and second segments, preferably the first segment, extends at least partly or entirely, in radial direction to said first longitudinal axis, preferably from its inlet (opening) on, i.e. from its start on, relating to flow direction. Furthermore, at least one of said mixing channels may further comprise additionally at least a third segment.

With a mixing nozzle comprising at least one inlet channel extending at least partly arc-shaped and at least one mixing channel extending at least partly in radial direction an advantageous flow behaviour for mixing of the liquid compositions can be achieved in the mixing channel, in particular, if said arc-shaped inlet channel segment runs into the radial extending segment of the mixing channel.

Preferably, at least two arc-shaped extending segments of said inlet channels merge into each other and merge simultaneously into at least one of said mixing channel, wherein preferably said mixing channel at least partly or entirely extends in radial direction, particularly from its inlet (opening) on. This results in a very beneficial flow behaviour, in particular a very beneficial mixing flow behaviour, can be achieved within the mixing zone, particularly in said mixing channel.

Preferably, at least one of the second segments of at least one of said mixing channels is arranged in flow direction behind a first segment of said mixing channel.

Preferably, at least one of the first segments of at least one mixing channel starts at the inlet (opening) of said mixing channel, i.e. at least one first segment preferably starts at the inlet of said mixing channel. Preferably, at least one of the first segments of at least one of said mixing channels abuts on an outlet of at least one of said inlet channels.

Preferably at least one of the second segments of at least one of said mixing channels abuts to an end of the first segment of said mixing channel. In an alternative embodiment of the mixing nozzle according to the present invention, one or more segments can be arranged between the first and second segment of at least one of said mixing channels.

In an embodiment of the mixing nozzle according to the present invention, the at least one segment of the mixing channel extending at least partly or entirely in radial direction runs at least partly meander-shaped, preferably in a plane parallel to said first longitudinal axis and/or in a plane perpendicular to said first longitudinal axis.

By a at least partly meander-shaped pathway a common flow path length, in particular a mixing distance, can be increased without increasing mixing nozzle length in the first longitudinal direction substantially. Hence, with a meander-shaped pathway mixing of the liquid compositions can be improved without substantial negative influence on ergonomics and/or handling of the application device.

In an embodiment of the mixing nozzle according to the present invention, at least one of said mixing channels, preferably at least one of the at least first and second segments of the mixing channel, particularly said first segment and/or said second segment of the at least one mixing channel, extends at least partly or entirely in a plane perpendicular to said first longitudinal axis.

This allows increasing the common flow path length, in particular the mixing distance, without increasing mixing nozzle length in the first longitudinal direction substantially. Hence, herewith mixing of the liquid compositions can be improved without substantial negative influence on ergonomics and/or handling of the application device.

In an embodiment of the mixing nozzle according to the present invention, at least one of the at least first and second segments of the at least one mixing channel, preferably said second segment of the at least one mixing channel, extends at least partly or entirely arc-shaped around said first longitudinal axis, preferably in a plane perpendicular to said first longitudinal axis. Herewith, the common flow path length, in particular the mixing distance, can be increased without substantially increasing the mixing nozzle length in the first longitudinal direction. Hence, mixing of the liquid compositions can be improved without any substantial negative impact on ergonomics and/or handling of the application device.

Alternatively and/or additionally to the extension in a plane perpendicular to said first longitudinal axis, at least one of said arc-shaped segments of said at least one mixing channel may at least partly or entirely extend arc-shaped along an inner lateral surface of a cone, in particular along an inner lateral surface of a rotationally symmetric cone, preferably of a cone with its cone tip on said first longitudinal axis. This can be advantageous in some applications, in particular regarding package and/or flow behaviour within said mixing channel.

Preferably, at least one of said arc-shaped segments of at least one of said mixing channels extends at least partly or entirely circle-arc-shaped, particularly circle-arc-shaped around said first longitudinal axis. With a circle-arc-shaped inlet channel in a lot of use cases flow homogeneity can be improved, in particular an extra homogeneous flow, particularly a more laminar flow can be achieved.

Preferably, at least one of said arc-shaped segments of at least one of said mixing channels extends arc-shaped about a circumferential angle of at least 30, 60 or 90 degrees up to an angle of maximum 90, 120, 150, 180, 270 or 300 degrees, particularly with a circumferential angle of 270 degrees.

Herewith, beneficial effects regarding mixing results in a lot of use cases can be achieved, in particular a mixing nozzle with a sufficient mixing distance can be conveniently provided.

Preferably, in particular for further improvement of mixing flow behaviour and/or to avoid dead zones, the mixing nozzle comprises flow manipulating elements, particularly alternating arranged manipulating elements, in at least one arc-shaped or extending along a n-cornered, in particular hexagonal or octagonal contour, or extending a star-shaped segment of at least one of said mixing channels, wherein a flow manipulating element can be a protrusion, flow splitting element, impact element, slot, grid, ramp, inclined wall and or declined wall or can comprise one or more protrusions, flow splitting elements, impact elements, slots, grids, ramps, inclined walls and/or declined walls.

Particularly, the mixing nozzle comprises one or more flow manipulating elements arranged alternating in at least one of said mixing channels as impact elements and/or flow splitting elements and/or ramps, wherein preferably at least one flow manipulating element is configured to split the flow within the mixing channel and/or to cause a defined back flow and/or a defined helical flow in the mixing channel to improve mixing.

The mixing nozzle may further preferably comprise at least one static mixing element as known in prior art extending along the first longitudinal axis, wherein said static mixing element is preferably arranged within the outlet channel. This may be necessary or desired in some cases to achieve sufficient mixing results, but is, however, not preferred because of increasing mixing nozzle length in longitudinal direction.

In an embodiment of the mixing nozzle according to the present invention, the mixing nozzle comprises connection means for connecting an injection needle to the mixing nozzle, wherein in an established connection between the mixing nozzle and said injection needle the outlet channel of the mixing nozzle is fluidly connected to a lumen of the injection needle, and wherein said connection means of the mixing nozzle is preferably rotatable around the first longitudinal axis to adjust needle orientation relatively to the mixing nozzle and/or the application device.

Preferably, the mixing nozzle is detachably connectable or can be detachable mounted to a multi-component application device, preferably by at least one snap-fit connection. The term "connection means", as used herein, refers to means for establishing a connection, in particular for establishing a fluid connection.

In an embodiment of the mixing nozzle according to the present invention, said connection means of the mixing nozzle is a Luer connector, preferably a Luer-cone connector (Luer-slip connector) or a Luer-lock-connector, wherein in an established Luer-cone connection respectively in an established Luer-lock-connection between the mixing nozzle and the injection needle the outlet channel of the mixing nozzle is fluid connected to the lumen of the injection needle. With a Luer connector the fluid connection between the outlet channel of the mixing nozzle and the lumen of an injection needle can be established in a very easy manner. A Luer-lock connector has compared to the Luer-cone connector the advantage that a more safe and locking connection, which is also releasable, can be established.

Luer connections and connectors are generally known in prior art and standardised, wherein Luer connections generally comprise a male Luer connector and a corresponding female Luer connector. Luer-cone connections are for example described in DIN EN 20594-1:1995-01 and Luer-lock connections in DIN EN 1707:1997-01. Both are characterized by a special 6% cone, wherein a Luer-lock connection additionally comprises a threaded connection.

A mixing nozzle comprising a Luer connector allows the connecting with several injections needles, manufacturer independent to the mixing nozzle and the establishment of safe, leak-proof and sterile connections in an easy manner.

As used herein, the term "needle orientation" refers to the orientation of an injection needle's orifice relatively to skin surface, in particularly it refers to the orientation of an injection needle's bevel or cut relatively to skin surface, preferably at the time of access or puncture during injection procedure.

It is known, that "needle orientation", i.e. the orientation of its bevel preferably at the time of access or puncture during injection procedure, has at least an influence on pain, insertion forces, tissue deformation and tissue trauma. Needle's bevel orientation parallel to the skin is preferably used for the so called "blanching-technique", which is a special technique for intradermal injection of a dermal filler beneath the skin surface to improve skin texture.

If an application device or an application device is used for injection with an injection needle connected by a Luer-lock-connection to the body, the whole application device has to be rotated together with the needle around its longitudinal axis to achieve optimal bevel orientation, to avoid releasing of the Luer-lock connection by needle rotation relatively to the body of the application device.

Particularly, if the application device comprises a finger grip or handle extending in a direction perpendicular to the longitudinal axis of the injection needle, wherein the terms "handle" and "finger grip" herein are used interchangeable, rotation around the longitudinal axis of the needle to optimize bevel orientation is not possible without increasing the injection angle in some application cases, particularly in cases of intradermal or subcutaneous injections, where small injection angles of 5 up to 15 degrees are necessary.

With rotatable connection means, also by using a Luer-lock connection for connecting the injection needle, the needle can be rotated relatively to the mixing nozzle and/or the application device after connection to the mixing nozzle along its longitudinal axis without rotation of the whole application device. Hence, with a mixing nozzle according to the invention comprising rotatable connections means optimal bevel orientation can be achieved without rotation of the whole application device, also in application cases requiring small injections angles as for example in the case of intradermal or subcutaneous injections.

Preferably, the mixing nozzle comprises, particularly releasable, locking means, to lock said connection means after adjusting needle orientation to fix optimized needle orientation position.

In an embodiment of the mixing nozzle according to the present invention, the mixing nozzle is assembled of at least a first part and a second part, particularly of at least three parts (a first, a second and a third part), wherein a joint between said first part and said second part passes at least partly through the mixing nozzle adjacent to said mixing channel and/or at least partly within said mixing channel.

Preferably, the mixing nozzle comprises or is made of at least two different materials, in particular by two-component injection molding, wherein in particular that part of the mixing nozzle being configured for coupling to the body of an application device comprises at least one less rigid material, preferably an elastomeric material such as rubber and/or silicon and/or TPE, e.g., to optimize sealing between the inlet channels of the mixing nozzle and the outlet channels of the chambers or containers of the body, wherein the part being configured for connection to an injection needle generally comprises or is made of a more rigid material, preferably of ABS, POM, PC, SAN and/or PP.

With a nozzle designed like outlined above, the joint between said first part and said second part arranged passing at least partly through the mixing nozzle adjacent to said mixing channel and/or at least partly or entirely within said mixing channel manufacturing of the nozzle can be done in an easy way. Particularly, in that area, in which the joint between the first part and the second part passes adjacent to the mixing channel and/or within the mixing channel, in each die only protrusions instead of cores are necessary to form the cavity of the mixing zone.

In some embodiments of a mixing nozzle and/or an application device according to the present invention, according to the further invention and/or according to the yet further invention, at least said first part and said second part of the mixing nozzle, in particular at least first, second and third parts or all parts of the nozzle, may be welded, e.g. sonic welded, laser-welded or friction welded, and/or glued and/or joint together by multi-component injection moulding. All or some of the nozzle parts can also alternatively or additionally be connected by at least one snap-fit connection.

In a second aspect, the present invention relates to a multi-component application device, particularly a two-component application device, for discharging a liquid mixed composition of at least a first liquid composition and a second liquid composition and for injection of the liquid mixed composition, which is configured to separately store the first and second liquid compositions in the application device and to mix the first and second liquid compositions before injection into a target site of a human body, wherein the application device comprises a mixing nozzle according to the present invention.

In an embodiment of the application device according to the present invention, the application device comprises, in addition to the mixing nozzle according to the present invention, a body, a plunger assembly and a handle, wherein said handle preferably comprises two wings extending in opposite directions radially outwards from said body relating to said first longitudinal axis, and wherein said handle is rotatable around said first longitudinal axis to adjust handle orientation relatively to said mixing nozzle and/or said body.

With a handle rotatable around the first longitudinal axis adjusting of the handle relative to the mixing nozzle and therefore to a needle connected to the mixing nozzle is possible, in particular optimum adjustment of the handle relative to needle orientation, respectively to needle's cut can be achieved.

Preferably, the handle is rotatable around the first longitudinal axis without causing a plunger assembly movement. For handle rotation relatively to the body, preferably in or on the body at or near its distal end an insert, in particular a disc-shaped rim, is arranged, which has preferably been inserted into the body from its distal end or which has been mounted onto the body on its distal end, wherein the insert serves as a carrier for the handle and is configured for enabling rotation of the handle relatively to the body. Preferably the insert is mounted non-rotatable to the body.

As used herein, the term "body" refers to a carrier element or carrier assembly either comprising at least two chambers, each fillable or pre-filled with one of the liquid compositions to be mixed, or being configured to receive at least two containers, each fillable or pre-filled with one the liquid compositions to be mixed.

The term "plunger assembly", as used herein, refers to a device for dispensing the contents, in particular the liquid compositions, out of the chambers or containers, wherein the plunger assembly preferably is configured to dispense them simultaneously, such that the appropriate mixing ratio of the liquid compositions will be preserved.

The term "handle", as used herein, refers to a grasping device, in particular to a grasping device for supporting a first finger and a second finger of a medical practitioner at using the application device, wherein the terms "handle" and "finger grip" are used herein interchangeably.

In an embodiment of the application device according to the present invention, the plunger assembly comprises at least two plungers, one for each chamber or container, wherein the plungers preferably either are connected, particularly at their distal ends, by a thumb plate which is particularly snap-fit connected to the plungers, or are integrally manufactured with said thumb plate, wherein the thumb plate preferably is configured for supporting a thumb of a medical practitioner at using the application device.

The application device may be a double-application device in the form of a syringe having two integrally connected syringes, i.e. two integrally connected barrels, and a mono or double plunger assembly for dispensing the contents from the barrels. Also, the syringe system may include two detachably connected barrels and two or one detachably connected plungers.

Preferably, the mixing nozzle is arranged near or at a proximal end of said body and the handle is arranged near or at a distal end of said body.

In an embodiment of the application device according to the present invention, said mixing nozzle is detachable mounted to said body, preferably by at least one snap-fit connection, wherein the application device particularly comprises at least one actuation means for releasing said snap-fit connection, wherein said actuation means is preferably arranged in said mixing nozzle or in said body, particularly in said body. With the arrangement of the actuation means in the body a benefit regarding package within the mixing nozzle can be achieved. In particular, marginally package is needed for the actuation means in the mixing nozzle. Hence, the existing package can be used for mixing, i.e. for the mixing zone.

In a preferred embodiment of the application device according to the present invention, the mixing nozzle is detachably mounted to the body by at least two snap-fit connections, which have to be released simultaneously to avoid unintended releasing of the mixing nozzle.

In some embodiments of a mixing nozzle and/or an application device according to the present invention, according to the further invention and/or according to the yet further invention, the snap-fit connection for releasable detaching the mixing nozzle to the body may be arranged in the mixing nozzle and at least two nozzle parts, in particular at least three nozzle parts, may also be connected by a snap-fit connection. Preferably, said two snap-fit connections are both coupled, in particular operatively connected, wherein preferably their actuation means are coupled. Thereby, a package-saving connection between mixing nozzle and body can be realised.

The term "snap-fit-connection", as used herein, refers to a connection, which can be established by at least one locking hook being configured to be placed behind a corresponding configured locking protrusion and/or undercut.

In a third aspect, the present invention relates to a kit comprising a mixing nozzle according to the present invention or an application device according to the present invention.

The kit preferably comprises an application device according to the present invention, wherein the mixing nozzle is provided separately, i.e. unmounted respectively not connected to the body of the application device.

Preferably, the application device further comprises a body, a plunger assembly and a handle, wherein particularly, the handle and the plunger assembly are assembled with the body.

Optionally, the kit can comprise instructions for use. The "instructions for use" may, for example, be instructions for use in cosmetic applications and/or for injecting a soft tissue filler (e.g. a dermal filler) into the human body, including replacing or filling of a biological tissue or increasing the volume of a biological tissue for the purpose of cosmetic applications. In particular, the kit may comprise instructions for use as a soft tissue filler or a dermal filler in cosmetic treatments.

In an embodiment of the kit according to the present invention, the kit further comprises a first liquid composition A and a second liquid composition B, the first liquid composition A and the second liquid composition being capable of forming an in situ crosslinkable dermal filler composition, wherein the first liquid composition A and the second liquid composition B are stored separately in the kit.

Preferably, the first and second liquid composition are each stored in an generally exchangeable container, particularly in an generally exchangeable mono-chamber syringe, either inserted or insertable into the body or carried or receivable by the body. However, in most use cases, i.e. in most embodiments, it is preferred, to provide the kit with already inserted containers, which preferably may not be exchanged by a user, particularly not without destroying a predetermined breaking point.

Furthermore, at least one of the containers, preferably both, may comprise connection means, in particular a male Luer-cone connector or a male Luer-lock connector, for establishing a fluid connection to one of the inlet channels of the mixing nozzle by connecting with a corresponding connection means of the mixing nozzle.

In addition, at least one container or chamber outlet opening is preferably covered by protection means, in particular by a protection tip cap, in order to seal the outlet channels of the chamber and or container to avoid contamination. The chambers and containers generally have the storage capacity for containing enough of the first and second liquid compositions. The body and/or the chambers and/or containers may be made of glass, plastic or any other suitable material and may have different geometries, inner diameters, material compositions, clearness, etc.

In an embodiment of the kit according to the present invention, the first liquid composition A is preferably a solution of a polysaccharide derivative functionalized with a first reactive group, in particular a nucleophilic group, and the second liquid composition B is preferably a solution of a polysaccharide derivative functionalized with a second reactive group, in particular an electrophilic group. The nucleophilic group and the electrophilic group are capable of forming a covalent linkage in situ following co-injection of the first and second polysaccharide derivatives to a target site in the human body, resulting in the in situ formation of a cross-linked hydrogel at the target site. Particularly preferred, the first liquid composition A is a solution of a first hyaluronic acid (HA) derivative functionalized with said first reactive group, in particular a solution of a hydrazide functionalized first hyaluronic acid (HA) derivative, and the second liquid composition B is a solution of a second hyaluronic acid (HA) derivative functionalized with said second reactive group, in particular a solution of an aldehyde functionalized second hyaluronic acid (HA) derivative.

Mixing of said first first liquid composition A and said second liquid composition B rapidly and efficiently results in cross-links in situ to form a covalently cross-linked hydrogel at the target site in the body. Preferably, no additives, no catalysts, no pH switch, no UV irradiation nor any other external stimuli (or "triggers") are required to induce the cross-linking reaction. In particular, preferably no cross-linker is used or required.

The first and second polysaccharide derivatives are usually both sterilized. The term "sterilized" or "sterile", as used herein, is intended to refer to heat sterilization, in particular moist heat sterilization (e.g., steam sterilization), and preferably refers to autoclaving. Autoclaving may be carried out at a temperature of 120° C. to 137 C for 2.0 min to 20 min, or at 121° C. to 130° C. for 2.0 min to 20 min, e.g. at 127° C. for 6.0 min or 134° C. for 4 min. The amount of the first polysaccharide derivative present in the first liquid composition may be from 0.1 wt. % to 5.0 wt. %, and the amount of the second polysaccharide derivative present in the second liquid composition may be from 0.1 wt. % to 5.0 wt. %. Moreover, the weight ratio of the co-injected first and second polysaccharide derivative is preferably from 15:85 to 85:15, more preferably 40:60 to 60:40 or 50:50 (first derivative to second derivative).

Furthermore, the first and/or second liquid compositions may comprise additional substances such as cells, including stem cells, and adipocytes, fat, lipids, growth factors, cytokines, drugs, and bioactives. More specifically, the first and/or second liquid compositions may comprise local anesthetic agents (e.g. lidocaine), polyalcohols, vitamins, alkali metal and alkaline earth metal salts, metals, antioxidants, amino acids, peptides, proteins (e.g., neurotoxins) and ceramic particles. For further details and preferred embodiments of the liquid compositions A and B reference is made to WO 2017/063749.

It is pointed out that the present invention also contemplates the provision of a multi-component application device (e.g., a two-component application device), in particular a multi-component syringe assembly (e.g., a two-component syringe assembly), of the present invention and described in detail herein, which is filled with the at least first and second liquid compositions as described herein. In other words, the present invention also relates to a pre-filled multi-component application device. Such a pre-filled multi-component application device may also be comprised in the kit according to the present invention.

In one embodiment of present invention, the kit further comprises two tip caps and a tip cap remover, wherein the two tip caps each are covering at least partly one of the connection means of the application device being configured for being coupled to the mixing nozzle, and wherein the tip cap remover is configured for removing the two tip caps simultaneously.

In one embodiment of present invention, the tip cap remover comprises two clamps and a flap, which can be locked in closing-position by a snap-fit connection, wherein the tip cap remover preferably further comprises a grip.

In another, in particular alternative, embodiment of present invention the tip cap remover comprises clamping means and is configured such that it can be deformed elastically, preferably compressed elastically, by pressing the clamping means towards each other by a user for clamping the caps in between for grabbing and removing them simultaneously.

In a fourth aspect, the present invention relates to a method for cosmetic or therapeutic treatment or application, particularly for replacing or filling a biological tissue or increasing the volume of a biological tissue, wherein an effective amount of an injectable liquid composition, particularly an injectable dermal filler composition, is to be administered or is administered to a subject by using an application device according to the present invention and/or a kit according to the present invention.

The dermal filler composition of the present invention may generally be administered in an effective amount to a subject by injection, such as by subcutaneous or intradermal injection. For example, the composition may be intradermally or subcutaneously injected using the serial puncture technique, preferably with an injection angle of minimum 5, 8, or 10 degrees up to an injection angle of maximum 12 or 15 degrees. The term "injection angle", as used herein, refers to the angle between said first longitudinal axis of the injection needle and the line projected by the needle onto the skin surface.

The term "effective amount" refers to the amount of the (injectable) soft tissue filler composition sufficient to effect beneficial or desired cosmetic (aesthetic) results. A "subject", as used herein, may be any individual or patient, e.g., a mammal and, preferably, a human, in need of a treatment or application for cosmetic (aesthetic) purposes.

Further described herein is a further invention which, however, is not subject of the appended claims.

In a first aspect according to the further invention, there is provided a nozzle for an application device, preferably for injection of a liquid composition, wherein the nozzle comprises at least one fluid inlet channel for receiving at least one fluid to be discharged, an outlet channel being connectable to an injection needle having a lumen extending along a first longitudinal axis, wherein said outlet channel of the nozzle is fluidly connected or connectable with said inlet channel, wherein the nozzle comprises connection means for connecting an injection needle to the nozzle, and wherein said connection means of the nozzle is rotatable around said first longitudinal axis to adjust needle orientation relatively to the nozzle and/or to the application device.

In an embodiment of the nozzle according to the further invention, the nozzle is a mixing nozzle for a multi-component application device for mixing at least a first liquid composition and a second liquid composition stored separately in an application device, particularly for a two-component application device for injection, in particular intradermal injection, of a dermal filler composition.

In an embodiment of the nozzle according to the further invention, the nozzle further comprises at least one feature described in this application related to the mixing nozzle according to the present invention.

In a second aspect of the further invention, there is provided an application device, preferably a multi-component application device, and more preferably a two-component application device, for discharging a liquid mixed composition of at least a first liquid composition and a second liquid composition and for injection of the liquid mixed composition, wherein the application device comprises a nozzle according to the further invention.

In an embodiment of the application device according to the second aspect of the further invention, the application device further comprises at least one feature described in this application related to the application device according to the present invention.

In a third aspect according to the further invention, there is provided a kit, comprising a nozzle according to the further invention or an application device according to the further invention. Preferably, the kit according to the third aspect of the further invention further comprises at least one feature described in this application related to the kit according to the present invention.

In a fourth aspect according to the further invention, there is provided a method for cosmetic or therapeutic treatment or application, particularly for replacing or filling a biological tissue or increasing the volume of a biological tissue, wherein an effective amount of an injectable liquid composition, particularly an injectable dermal filler composition, is to be administered or is administered by using an application device according to the further invention and/or a kit according to the further invention.

In an embodiment of the method according to the fourth aspect of the further invention, the method is further defined by at least one feature and/or further comprises at least one more step described in this application related to the present invention, in particular related to the method according to the fourth aspect of the present invention.

Further described herein is a yet further invention which, however, is not subject of the appended claims.

In a first aspect according to the yet further invention, there is provided an application device, preferably a multi-component application device, and particularly a two-component application device, for discharging a liquid mixed composition of at least a first liquid composition and a second liquid composition and for injection of the liquid mixed composition, in particular of a dermal filler composition, wherein the application device comprises a body, a plunger assembly and a handle, wherein said handle is rotatable around a longitudinal axis of the body to adjust handle orientation relatively to said body.

In an embodiment of the application device according to the first aspect of the yet further invention, the application device comprises an outlet channel, wherein said outlet channel is connectable to a lumen of an injection needle extending along a first longitudinal axis. Preferably, in a connected state, i.e. when an injection needle is connected to the nozzle, the longitudinal axis of the body is parallel to said first longitudinal axis of said injection needle, particularly concentric.

In an embodiment of the application device according to the first aspect of the yet further invention, the application device comprises a nozzle according to the present invention and/or according to the further invention.

In an embodiment of the application device according to the first aspect of the yet further invention, the application device further comprises at least one feature described in this application related to the application device according to the present invention and/or to the further invention.

In a second aspect according to the yet further invention, there is provided a kit, comprising a nozzle according to the present invention and/or to the further invention and/or an application device according to the yet further invention.

In an embodiment of the kit according to the second aspect of the yet further invention, the kit further comprises at least one feature described in this application related to the kit according to the present invention and/or to the further invention.

In a third aspect according to the yet further invention, there is provided a method for cosmetic or therapeutic treatment, particularly for replacing or filling a biological tissue or increasing the volume of a biological tissue, comprising administering to a subject in need thereof an effective amount of an injectable liquid composition, particularly an injectable dermal filler composition, by using an application device according to the yet further invention and/or a kit according to the yet further invention.

In an embodiment of the method according to the third aspect of the yet further invention, the method is further defined by at least one feature and/or further comprises at least one more step described in this application related to the present invention and/or the further invention, in particular related to the method according to the fourth aspect of the present invention and/or according to the fourth aspect of the further invention.

The inventions described above, in particular the present invention, will now be further explained by the following, non-limiting embodiments and examples, wherein further optional features of the inventions are disclosed in the drawings and in the description of these drawings. All features and all combinations of features described above and/or outlined below and/or only illustrated in the drawings can be realized in an embodiment of the inventions in the combination described or stand alone or in at least one other combination not described explicitly herein, as this combination is technically reasonable.

BRIEF DESCRIPTION OF THE DRAWINGS

FIG. 1a a cross-sectional view of a section along plane A-A of a first embodiment of an application device, i.e. a syringe assembly, according to the present invention and/or the further invention with a first embodiment of a mixing nozzle according to the present invention, FIG. 1b a front plane view of the syringe assembly of FIG. 1a, FIG. 1c a side plane view of the syringe assembly of FIGS. 1a and 1b, FIG. 1d a cross-sectional view of a section along plane B-B of the syringe assembly of FIGS. 1a, 1b and 1c, FIG. 1e a top view of the syringe assembly of FIGS. 1a, 1b, 1c and 1d, FIG. 2 a perspective view of the distal part of the mixing nozzle of the syringe assembly of FIG. 1a to 1e, FIG. 3a a cross-sectional view of a second embodiment of a mixing nozzle according to the present invention, FIG. 3b a perspective explosion view of the mixing nozzle of FIG. 3a, FIG. 4a a cross-sectional view of the section along plane A-A of the mixing nozzle of the syringe assembly of FIG. 1a to 1e, FIG. 4b a front plane view of the mixing nozzle of FIG. 4a, FIG. 4c a side plane view of the mixing nozzle of FIGS. 4a and 4b, FIG. 4d a cross-sectional view of a section along plane B-B of the mixing nozzle of FIGS. 4a, 4b and 4c, FIG. 4e a top view of the syringe assembly of the mixing nozzle of FIGS. 4a, 4b, 4c and 4d, FIG. 5a the cross-sectional view of the section along plane A-A of the syringe assembly of FIG. 1a to 1e without the mixing nozzle and the plunger assembly in a state as preferably provided in a kit according to the present invention, the further invention and/or the yet further invention, FIG. 5b a front plane view of the parts of the syringe assembly of FIG. 5a, FIG. 5c a side plane view of the parts of the syringe assembly of FIGS. 5a and 5b, FIG. 5d a cross-sectional view of a section along plane B-B of the parts of the syringe assembly of FIGS. 5a, 5b and 5c, FIG. 5e a top view of the syringe assembly of the parts of the syringe assembly of FIGS. 5a, 5b, 5c and 5d, FIG. 6a a cross-sectional view of the section along plane A-A of the plunger assembly of the syringe assembly of FIG. 1a to 1e, FIG. 6b a front plane view of the plunger assembly of FIG. 6a, FIG. 6c a side plane view of the plunger assembly of FIGS. 6a and 6b, FIG. 6d a cross-sectional view of a section along plane B-B of the plunger assembly of FIGS. 6a, 6b and 6c, FIG. 6e a top view of the syringe assembly of the plunger assembly of FIGS. 6a, 6b, 6c and 6d, FIG. 7a a cross-sectional view of the section along plane A-A of a second embodiment of an application device, i.e. a syringe assembly, according to the present invention and/or the further invention with a third embodiment of a mixing nozzle according to the present invention, FIG. 7b a front plane view of the syringe assembly of FIG. 7a, FIG. 7c a side plane view of the syringe assembly of FIGS. 7a and 7b, FIG. 7d a cross-sectional view of a section along plane B-B of the syringe assembly of FIGS. 7a, 7b and 7c, FIG. 7e a top view of the syringe assembly of FIGS. 7a, 7b, 7c and 7d, FIG. 7f a perspective view of the syringe assembly of FIGS. 7a, 7b, 7c, 7d and 7e, FIG. 7g a perspective view of the syringe assembly of FIG. 7a, 7b, 7c, 7d, 7e und 7f in a state with a handle rotated relatively to the body, FIG. 8a a cross-sectional view of the section along plane A-A of the mixing nozzle of the syringe assembly of FIG. 7a to 7g, FIG. 8b a front plane view of the mixing nozzle of FIG. 8a, FIG. 8c a side plane view of the mixing nozzle of FIGS. 8a and 8b, FIG. 8d a cross-sectional view of a section along plane B-B of the mixing nozzle of FIGS. 8a, 8b and 8c, FIG. 8e a top view of the syringe assembly of the mixing nozzle of FIGS. 8a, 8b, 8c and 8d, FIG. 9a the cross-sectional view of the section along plane A-A of the syringe assembly of FIG. 7a to 7g without the mixing nozzle and the plunger assembly in a state as preferably provided in a kit according to the present invention, the further invention and/or the yet further invention, FIG. 9b a front plane view of the parts of the syringe assembly of FIG. 9a, FIG. 9c a side plane view of the parts of the syringe assembly of FIGS. 9a and 9b, FIG. 9d a cross-sectional view of a section along plane B-B of the parts of the syringe assembly of FIGS. 9a, 9b and 9c, FIG. 9e a top view of the syringe assembly of the parts of the syringe assembly of FIGS. 9a, 9b, 9c and 9d, FIG. 10 a cross-sectional view of a fourth embodiment of a mixing nozzle according to the present invention, FIG. 11a a first perspective view of a distal part of a fifth embodiment of a mixing nozzle according to the present invention, FIG. 11b a second perspective view of the distal part of FIG. 11a, FIG. 12a a cross-sectional view of a detail of a third embodiment of an application device, i.e. a syringe assembly, with a sixth embodiment of a mixing nozzle according to the present invention and/or the yet further invention, FIG. 12b the syringe assembly of FIG. 12a with connected injection needle in injection position in a state with non-adjusted needle orientation, FIG. 12c in zoom view the injection needle's tip (bevel) of the injection needle of FIG. 12b in injection position with non-adjusted needle orientation, FIG. 12d the syringe assembly of FIG. 12a to 12c with connected injection needle in injection position in a state with adjusted needle orientation, FIG. 12e in zoom view the injection needle's tip (bevel) of the injection needle of FIG. 12b in injection position with non-adjusted needle orientation, FIG. 13 an explosion view of a fourth embodiment of an application device according to the present invention and/or the yet further invention with a seventh embodiment of a mixing nozzle according to the present invention, FIG. 14 a detailed explosion view of the application device of FIG. 13 without the mixing nozzle, FIG. 15 the mono-chamber syringe holder of the application device of FIGS. 13 and 14 in a perspective view in detail, FIG. 16 the backstop plate of the application device of FIGS. 13 and 14 in a perspective view in detail, FIG. 17 the tip cap remover of the application device of FIGS. 13 and 14 in a perspective view in detail, FIG. 18a the mixing nozzle of FIG. 13 in an explosion view, FIG. 18b the distal nozzle part of the mixing nozzle of FIGS. 13 and 18a in a perspective view in detail, FIG. 18c a bottom view of the distal nozzle part of the mixing nozzle of FIGS. 13, 18a and 18b, FIG. 19 the explosion view of the fourth embodiment of an application device of FIG. 14 supplemented by directional arrows for visualization of partial assembly of said application device, FIG. 20a-20i several explosion views of several parts of the fourth embodiment of an application device of FIGS. 13, 14 and 19 for visualization of several single steps of assembly of said application device in detail, FIG. 21a a further embodiment of a tip cap remover coupled to the caps of two mono-chamber syringes being arranged in a body of an application device, FIG. 21b the tip cap remover of FIG. 21a before coupling to the caps, and FIG. 22 to 28 several mixing geometries of mixing zones for further embodiments of a mixing nozzle according to the present invention.

DETAILED DESCRIPTION OF A PREFERRED EMBODIMENT

Figure 7G:
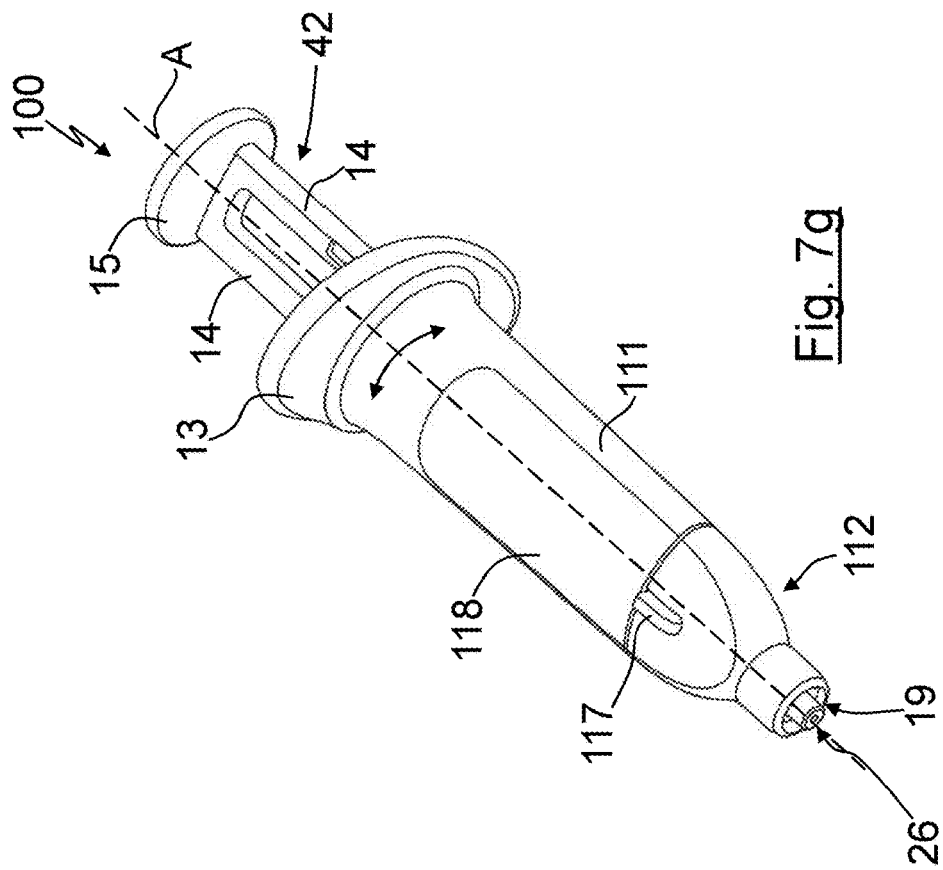

FIGS. 1a to 1e show different views of a first embodiment of an application device 10 according to the present invention and also according to the further invention, wherein the application device 10 in this case is a two-component syringe assembly 10.

The syringe assembly 10 is configured for discharging a mixed composition of a first liquid composition LC1 and a second liquid composition LC2. In particular, this two-component syringe assembly 10 is configured for intradermal injection of a dermal filler composition comprising a first liquid composition LC1 and a second liquid composition LC2.

The multi-component syringe assembly 10 is configured to separately store the first and second liquid compositions LC1 and LC2 and to mix the first and second liquid compositions before injection into a target immediately. Therefore, the syringe assembly 10 comprises a first embodiment of a mixing nozzle 12 according to the present invention.

The syringe assembly 10 further comprises a body 11, a plunger assembly 42 and a handle 13.

According to the present invention, the mixing nozzle 12 comprises a first and a second fluid inlet channel 27, 28 for receiving the separately stored liquid compositions LC1 and LC2 to be mixed, a mixing zone 29, which is in FIG. 1a to 1e illustrated schematically only, having at least one mixing channel (non-referenced in FIG. 1a to 1e, see e.g. FIGS. 2 and/or 3b), for mixing the liquid compositions LC1 and LC2 while they flow through the mixing channel, and an outlet channel 26 connectable to an injection needle having a lumen extending along a first longitudinal axis A, wherein the outlet 26 channel of the mixing nozzle 12 is fluidly connected with the inlet channels 27, 28 of the mixing nozzle 12 by the mixing zone 29.

In this embodiment, the inlet channels 27, 28 extend at least partly parallel to the first longitudinal axis A, particularly from their inlet on respectively from their distal end on, wherein the outlet channel 26 extends entirely parallel to the first longitudinal axis A. The mixing zone 29 extends in a plane perpendicular to the first longitudinal axis A.

In this embodiment of the mixing nozzle according to the present invention, the mixing nozzle 12 further comprises connection means 19, particularly a Luer-lock-connector 19, for connecting an injection needle (not shown) to the mixing nozzle 12, wherein in an established connection between the mixing nozzle 12 and the injection needle the outlet channel 26 of the mixing nozzle 12 is fluidly connected to a lumen of the injection needle.

In this embodiment, the mixing nozzle 12 is assembled of a first, distal nozzle part 23A and a second, proximal nozzle part 23B, wherein a joint between said first part and said second part passes at least partly through the mixing nozzle 12 adjacent to the mixing zone 29, in particular at least partly adjacent to the mixing channel. The first, distal nozzle part 23A and the second, proximal nozzle part 23B are each made by injection moulding of a bio-compatible and sterilisable plastic material and are joint by sonic welding.

In this embodiment, the mixing nozzle 12 is detachable mounted to the body 11 by two snap-fit connections, each comprising locking hooks 31 and undercuts 32 as locking protrusions 32, wherein the snap-fit connections between the mixing nozzle 12 and the body 11 can be released by pressing actuation means 17 respectively release buttons 17. In this embodiment the actuations means 17 are arranged near the proximal end of the body 11 in the middle of the body 11. With this arrangement more available space in the mixing nozzle 12 for the mixing zone 29 can be provided compared to an arrangement of the snap-fit connections with its locking hooks 31, undercuts 32 and actuation means 17 in the mixing nozzle 12.

The release buttons 17 and the locking hooks 31 are integrally molded to a disc-shaped distal rim 20, which has been inserted into the body 11 in axial direction parallel to the first longitudinal axis A from a distal end of the body 11. The distal rim 20 extends substantially parallel to the first longitudinal axis A. The release buttons 17 and the locking hooks 31 are connected to that distal rim 20 by long elastically deformable arms, extending substantially along the first longitudinal axis A. Of course, in other embodiments, the snap-fit connections can have different geometries and different shapes.

In FIG. 1a to 1e the syringe assembly 10 is shown in a prefilled state, loaded with two standard mono-chamber syringes (containers) 24 and 25, each having a mono-chamber body 24A, 25B and a mono-chamber syringe tip 24B, 25B. Each tip 24B, 25B comprises a Luer-cone connector as connection means and an outlet channel 37, 38 for discharging the material stored in the corresponding container 24 respectively 25, particularly for discharging one of the liquid compositions LC1, LC2 out of the mono-chamber body 24A, 25B.

In this embodiment, the Luer-cone connection means of the syringe tips 24B and 25B of the two mono-chamber syringes 24 and 25 each interacts with corresponding connections means 39, 40 of the mixing nozzle (see FIG. 4a to 4e) for establishing a fluid connection between the outlet channel 37 of the mono-chamber syringe 24 and the inlet channel 27 of the mixing nozzle 12 respectively between the outlet channel 38 of the mono-chamber syringe 25 and the inlet channel 28 of the mixing nozzle 12.

In this embodiment, the syringe assembly 10 is configured to receive two standard single, i.e. separate, mono-chamber syringes 24, 25 each having a cut flange 24C, 25C at their distal end (see FIG. 5e), wherein the distal rim 20 interacts with the flanges 24C and 25C of the mono-chamber syringes 24, 25 and particularly serves as a holder and/or as positioning means for the two, standard mono-chamber syringes 24 and 25.

By retaining means 21, in particular by retaining plate 21, and by a proximal rim 34 axially movement of the two mono-chamber syringes 24 and 25, particularly dropping out from the distal end of the body 11, can be avoided.

In this embodiment, the syringe assembly 10 is configured to arrange the two standard single mono-chamber syringes 24, 25 each having a cut flange 24C, 25C with a close fit of the cut flanges 24C, 25C adjacent to each other to minimize width of the syringe assembly 10. Other arrangements are also possible, e.g. non-adjacent arrangement of the flanges of the mono-chamber syringes, spaced arrangement or offset arrangement.

In another embodiment (not shown herein), the syringe assembly is configured to receive at least two mono-chamber syringes with a full flange, i.e. with a round, non-cut flange.

In the embodiment shown in FIGS. 1a to 1e, the body 11 is configured to surround the mono-chamber syringes 24 and 25, i.e. all containers 24, 25, entirely in circumferential direction. In another embodiment, the body can be configured as a container carrier or a rack, e.g. similar or like the support member 31 described in the U.S. Pat. No. 7,883,501 B2.

For providing a multi-chamber application device with beneficial ergonomic handling, which allows very precise injections, in particular for intradermal and/or subcutaneous injections with injections angles α (see FIG. 12a to 12d) with less than 15 or less than 12 degrees, the body 11 has an oval or oval-like or rectangular or rectangular-like or elliptical or elliptical-like or at least partly flat cross-section profile as the body 11 has, wherein the broader side is orientated preferably to the skin side during injection. For this purpose, the body 11 comprises at least partly a substantially elliptical or oval cross-section in the area surrounding the two containers 24 and 25. In another embodiment, the body can comprise a different cross-section geometry, e.g. a circle-shaped cross-section, and/or be configured to surround the containers only partly.

In another embodiment of an application device, preferably for tolerance compensation along the first longitudinal axis A, i.e. in axial direction, at least one compensation means, preferably at least one spring mean, e.g. a coil spring or a spring washer, can be arranged between retaining plate 21 and at least one flange 24C, 25C of at least one of the mono-chamber syringes 24, 25.

In the illustrated embodiment of a syringe assembly 10 according to the present and further invention, both mono-chamber syringes 24 and 25 (container 24, 25) have been loaded pre-filled into the body 11 in an axial direction, that means parallel to the first longitudinal axis A from the distal end of the body 11. In another embodiment, the mono-chamber syringes can be loaded from a front side and/or lateral, wherein a body configured for front loading preferably comprises a cover plate removable for loading the containers.

In the illustrated embodiment of a syringe assembly 10 according to the present and further invention, the plunger assembly 42 comprises two plungers 14 connected by a thumb plate 15, which is integrally molded with the plungers 14, wherein the plungers are made of a bio-compatible and sterilisable plastic material. The plunger assembly 42 is slidable parallel to the first longitudinal axis A towards the proximal end of the body 11 for discharging the two liquid compositions LC1, LC2 out of the mono-chamber syringe bodies 24A, 25B simultaneously and mixing them by pressing them through the mixing nozzle 12. For this purpose, in this embodiment the proximal tips 43 each have an outer contour with snap-fit locking hooks (see FIGS. 6a to 6e) and are snap-fit connected to an appropriate formed piston 30, also made of a bio-compatible and sterilisable plastic material.

In another embodiment of a syringe assembly, the plungers 14 can be connected by a separate manufactured thumb plate, which can preferably be connected to the plungers 14 by at least one snap fit connection. In this case, the plungers may be connected to the pistons 30 by screwing alternatively, preferably before being connected by the thumb plate or by turning the mono-chamber syringe bodies 24A, 25A with the pistons 30 arranged inside.

FIG. 1a to 1e show the embodiment of the syringe assembly 10 in a state with a locked plunger assembly 42, in particular with locked plungers 14, wherein the plungers 14 are locked by removable locking means 16 in form of a locking clip 16 encompassing both plungers 14 against unintentional movement along the first longitudinal axis A towards the mixing nozzle 12 of the plunger assembly 42. In another embodiment, the locking means can be encompassing only one of the plungers 14 and/or can be inserted or put through at least one plunger 14. In another embodiment, the locking means can be mounted to at least one plunger 14 and/or the handle 13 in a state before use by a predetermined breaking point, which has to be broken and preferably be removed before use of the syringe assembly.

In the illustrated embodiment of a syringe assembly 10 according to the present and further invention, the handle 13 of the syringe assembly 10 comprises two wings extending in opposite directions radially outwards from said body 11 relating to the first longitudinal axis A. To provide a syringe assembly 10, which allows injections with injection angles α less than 15 degrees, in particular less than 12 degrees, with an ergonomic handling and therefore precise injections, the handle 13 is rotatable around the first longitudinal axis A to adjust handle orientation relatively to the mixing nozzle 12 and/or the body 11 to achieve optimal injection needle orientation respectively optimal bevel orientation of an injection needle connected to the mixing nozzle 12 (see e.g. FIGS. 7f and 7g, which show a second embodiment of a syringe assembly according to the present and further invention in a state without and with rotated handle 13).

In the embodiment of a syringe assembly 10 illustrated in FIG. 1a to 1e, the handle 13 of the syringe assembly 10 is rotatable without causing plunger assembly 42 movement around the first longitudinal axis A relatively to the distal rim 20, which is inserted into the body 11 and cannot be rotated relatively to the body 11. Of course, different constructions for providing an application device with a rotatable handle are possible.

To avoid pulling out of the plungers 14 of the mono-chamber syringe bodies 11 when moving them backwards, i.e. in direction towards the distal end of the body for aspiration means 11, in this embodiment, the plungers 14 each comprises a locking hook 33 interacting with the handle 13, wherein the handle 13 is assembled of two parts, of an upper part 13A and a lower part 13B, wherein the upper part 13A of the handle 13 acts as retaining means to stop plunger movement backwards. Of course, different constructions of locking means for preventing pulling out of the plunger assembly are possible.

In the embodiment of a syringe assembly 10 illustrated in FIG. 1a to 1e, each of the mono-chamber syringes 24, 25 may be at least partly filled, in particular at least partly pre-filled, with one of the liquid compositions LC1 and LC2, wherein the first mono-chamber syringe 24 may be at least partly pre-filled with a first liquid composition LC1 and the second mono-chamber syringe 25 may be at least partly pre-filled with the second liquid composition LC2.

In this embodiment, the first liquid composition LC1 may be a polysaccharide (e.g. hyaluronic acid) derivative functionalized with a nucleophilic group and the second liquid composition LC2 may be a polysaccharide (e.g. hyaluronic acid) derivative functionalized with an electrophilic group, wherein the first and second liquid compositions LC1 and LC2 are sterilized and are capable of in situ forming a crosslinkable dermal filler composition.

In the embodiment of a syringe assembly 10 illustrated in FIG. 1a to 1e, the body 11 of the syringe assembly 10 comprises at its front side and its back side each a transparent window 18 for surveillance of the amount administered during use of the syringe assembly 10. In another embodiment, the body comprises at least one side window, preferably arranged at its slim side.

In another embodiment, the syringe assembly, in particular the body, in particular the window, and/or the plungers comprise at least one scale, in particular with at least a 50% marker. In another embodiment, preferably additionally and/or alternatively, at least one of the mono-chamber syringe bodies comprises a scale, which is preferably readable through said window.

In one embodiment, the syringe assembly comprises two scales, one for each mono-chamber syringe, preferably wherein on one mono-chamber syringe or on the body adjacent to one mono-chamber syringe, one scale is arranged.

In another embodiment, in particular in an alternative embodiment, the syringe assembly comprises only one scale for both mono-chamber syringes, in particular a common scale for both mono-chamber syringes. This can be advantageous to avoid irritation of a user, which scale has to be read, particularly if there is some offset between the plunger rods and/or pistons of the two mono-chamber syringes.

FIG. 2 shows a perspective view of the distal part 23A of the mixing nozzle 12 of the syringe assembly 10 of FIG. 1a to 1e, wherein in this illustration geometry and pathway of the first inlet channel 27 and the second inlet channel 28 and of the mixing channel 22 respectively the mixing zone 29 are visible clearly. The mixing channel 22 defines a common flow path for the first liquid composition LC1 and the second liquid composition LC2, being discharged from the mono-chamber syringes 24 and 25 into the mixing nozzle 12.

In this embodiment, the first inlet channel 27 comprises a first segment 27A extending parallel to the first longitudinal axis A and a second, arc-shaped segment 27B. In this embodiment, the second inlet channel 28 also comprises a first segment 28A extending parallel to the first longitudinal axis A and a second segment 28B extending arc-shaped.

In this embodiment, said second arc-sharped segments 27B, 28B each extends arc-shaped in a plane perpendicular to the first longitudinal axis A in circumferential direction relating to the first longitudinal axis A about an angle of 90 degrees.

In this embodiment, second segments 27B and 28B of the first and second inlet channels 27 and 28 both merge tangentially into each other and run into the mixing zone 29, in particular into a first segment 22A of the mixing channel 22, which is in this embodiment extending in radial direction in the same plane perpendicular to the first longitudinal axis A as the second segments 27B and 28B of the two inlet channels 27 and 28 do.

In this embodiment, the mixing channel 22 further comprises a second segment 28B abutting at the end of the first segment 22A of the mixing channel, wherein the second segment 22B of the mixing channel extends arc-shaped in the same plane perpendicular to the first longitudinal axis A as the second segments 27B and 28B of the first and second inlet channels 27 and 28 do.

However, in this embodiment, the second segment 22B of the mixing channel 22 extends in circumferential direction about an angle of roundabout 300°, in particular for providing a sufficient pathway length for mixing the first liquid composition LC1 and the second liquid composition LC2 according to mixing requirements.

According to the present invention, to improve mixing, in particular to improve homogeneity of the mixed composition, flow manipulating elements 44, designed as ramps and flow splitters, which cause flow split and at least partly back flow, are arranged alternating within the mixing channel 22. By this flow manipulating elements 44 flow direction of a mixing flow can be changed at least partly alternating between at least a first flow direction and a second flow direction within the mixing channel. Thereby, turbulence and vortexes can be induced into the flow, whereby mixing, in particular homogeneity, can be improved.

In this embodiment, the mixing zone 29, respectively the mixing channel 22, further comprises a third segment 22C extending in radial direction in the same plane perpendicular to the first longitudinal axis A as the second segments 27B, 28B of the inlet channels and the second segment 22B of the mixing channel 22 do, wherein this third segment 22C of the mixing channel 22 runs into the outlet channel 26 at the center of the distal nozzle part 23A.

With the arc-shaped second segments 27B and 28B of the first and second inlet channels 27 and 28 moreover a swirl can be caused in the first radial extending segment 22A of the mixing channel 22 and further within the second, arc-shaped segment 22B of the mixing channel 22. Hence, mixing and/or homogeneity of the first and second liquid compositions LC1 and LC2 can be improved within the composition.

Furthermore, the mixing nozzle 12 provides an improved ease of application of a liquid composition, in particular a facilitated and more convenient injection of a liquid composition such as a hydrogel or an in situ crosslinkable dermal filler composition. Moreover, the mixing nozzle 12 of the present invention allows for a reduced risk of clotting and/or undesirable reaction of the materials in the mixing nozzle because of their beneficial mixing zone 29.

FIG. 3a shows a cross-sectional view of a second embodiment of a mixing nozzle 212 according to the present invention, wherein this mixing nozzle 212 is also manufactured of a distal nozzle part 223A and a proximal nozzle part 223B, wherein in this embodiment, the distal nozzle part 223A and the proximal nozzle part 223B are connected by a nozzle joining snap-fit connection 252 instead of a sonic welded joint as the mixing nozzle 12 described above comprises. In FIG. 3b a perspective explosion view of the mixing nozzle 212 of FIG. 3a is illustrated.

For ease of manufacturing, in particular for ease of injection molding of the distal nozzle part 223A and the proximal nozzle part 223B, the joint is also arranged at least partly within the mixing zone 29, wherein the mixing zone 229, has the same shape and geometry as the mixing zone 29 of the pre-described mixing nozzle 12. In particular, the arrangement of the flow manipulating elements 244 within the mixing zone 229 and their geometry are identical with them of the first embodiment of the mixing nozzle 12 according to the present invention and illustrated in FIG. 2.

In the embodiment illustrated in FIG. 3, the mixing zone 29 also extends in a plane perpendicular to the first longitudinal axis A. Furthermore, the first and second inlet channels 27 and 28 each also comprises at least one segment (not referenced here) extending at least partly arc-shaped.

However, the second embodiment of the mixing nozzle 212 according to the present invention differs from the pre-described mixing nozzle 12, in that the mixing nozzle 212 comprises connections means 219 without a Luer connector. The mixing nozzle 212 only comprises a cylindrical tip connector 219.

FIGS. 4a to 4e show different views of the mixing nozzle 12 of the syringe assembly 10 of FIG. 1a to 1e in detail, wherein in these illustrations several of the features of the mixing nozzle 12 explained above, are identifiable well.

To achieve sufficient sealing, particularly a secure sealing, between the mono-chamber syringe tips 24B, 25B and the mixing nozzle 12, particularly between the mono-chamber syringe tips 24B, 25B and the mixing nozzle's distal connections means 39, 40, in the illustrated embodiment, the mixing nozzle 12 comprises cup-shaped sealing inserts with radial protrusions 41, for interacting with the connection means of the mono-chamber syringe tips 24B, 25B.

In another embodiment of a mixing nozzle and/or a syringe assembly, to achieve sufficient sealing, at least one O-ring can be arranged for sealing of the connection between the mixing nozzle and the mono-chamber syringe tips 24B, 25B. Moreover, connection means can have different shapes and geometries.

FIGS. 5a to 5e show different views of the syringe assembly 10 of FIG. 1a to 1e without the mixing nozzle 12 and the plunger assembly 42 in a state as preferably provided in a kit according to the present invention, the further invention and/or the yet further invention, wherein in this state, the mixing nozzle 12 is preferably not mounted to the body 11 and wherein the mono-chamber syringe tips 24B and 25B are preferably covered by caps 35, 36 to avoid contamination of the liquid compositions LC1 and LC2 and/or the outlet channels 37, 38 of the mono-chamber syringes 24, 25.

Preferably, in a kit according to one of the described inventions, the mixing nozzle is provided sterilized, in particularly packaged by a sealing foil, wherein the distal end of the mixing nozzle is preferably sealed by a removable sealing cover film.

A method for assembling the kit, when the mixing nozzle 12 and the body 11 of said kit are not connected to each other and are provided as separate parts, comprises at least the step of mounting the mixing nozzle 12 to the body 11 by pushing the mixing nozzle 12 and the body 11 at least partly together along the first longitudinal axis A by establishing a connection between the mixing nozzle 12 and the body 11, in particular a snap-fit connection, wherein, if existing, caps 35, 36, and sealing package and/or cover from the mixing nozzle 12 have been removed before.

Further, for assembling a kit provided with a plunger assembly 42 separated from the mono-chamber syringes 24, 25, the plunger assembly 42 has to be assembled to the mono-chambers syringes 24, 25 by inserting the plungers 14 each into one of the mono-chamber syringe bodies 24A and 24B and connecting plunger tips 43 to the pistons 30 and secure plunger assembly 42 by upper handle part 13A and preferably by locking clip 16. If the plunger assembly 42 is also provided disassembled, it has also to be assembled before use.

In FIG. 5e, the cut flanges 24C and 25C of the mono-chamber syringes 24, 25 are identifiable very well, in particular their arrangement with the linear sides adjacent to each other for optimal package of the mono-chamber syringes within the body 11.

In FIG. 6a to 6e the plunger assembly of the syringe assembly of FIG. 1a to 1e is shown in different views, wherein in these illustrations several of the features of the plunger assembly 42 explained above are identifiable well.

FIGS. 7a to 7f show different views of a second embodiment of an application device 100 according to the present invention and/or the further invention, also designed as a syringe assembly 100, with a third embodiment of a mixing nozzle 112. This syringe assembly 100 differs from the first embodiment of the syringe assembly 10 in that point, that the actuation means 117 for releasing the snap-fit connection of the mixing nozzle 112 are arranged in the mixing nozzle 112 and not in the area of the body 111, wherein same parts as in FIG. 1a to 6e have same reference signs.

In this second embodiment of a syringe assembly 100 the actuation means 117 and locking hooks 131 are integrally molded to the distal part 123A of the mixing nozzle 112, wherein the distal part 123A of the mixing nozzle 112 is also sonic welded to the proximal part 123B of the mixing nozzle 112. The release buttons 117 are also arranged in the middle of the syringe assembly 100, in particular between the mono-chamber syringes 24, 25, and are also configured for interacting with corresponding formed locking protrusions 132 respectively undercuts 132 arranged at the proximal and of the body 111. The syringe assembly 100 also comprises a transparent window 118 with a scale (not shown) and a distal rim 120, inserted into the body 111 as a base for the cut flanges 24C and 25C of the mono-chamber-syringes 24 and 25 and as a base for handle 13, which is also configured being rotatable around the first longitudinal axis.

Figure 7F:
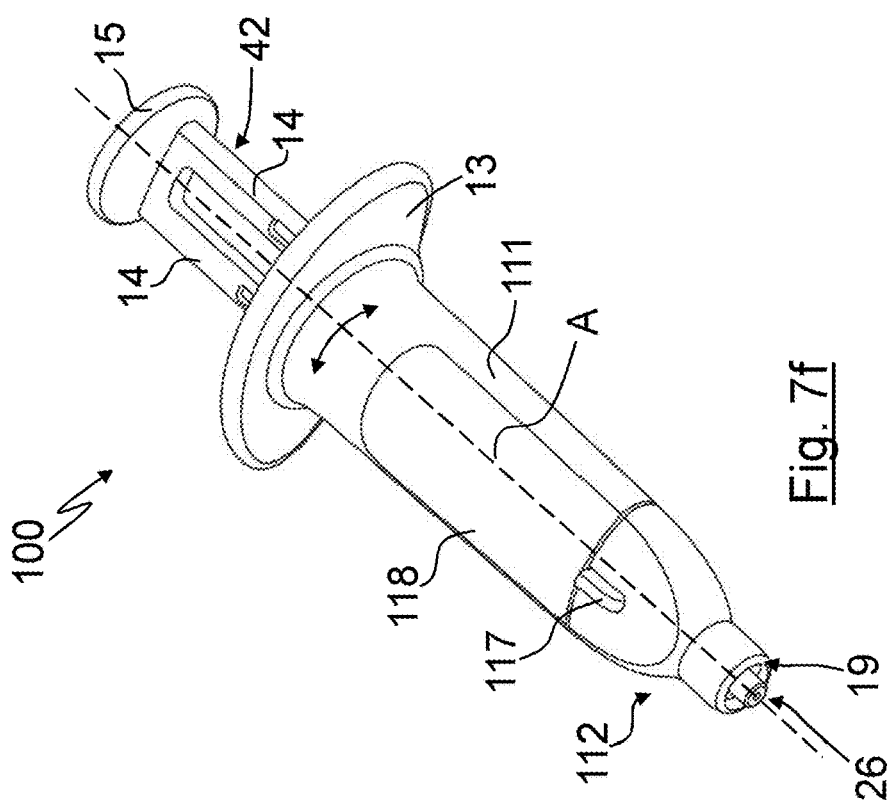

The handle 13 is also rotatable around the first longitudinal axis A to adjust handle orientation relatively to the mixing nozzle 112 and/or the body 111 to achieve optimal injection needle orientation respectively optimal bevel orientation of an injection needle connected to the mixing nozzle 112 (see e.g. FIGS. 7f and 7g, which show a second embodiment of a syringe assembly according to the present and further invention in a state without and with rotated handle 13).

The handle 13 of the syringe assembly 10 is rotatable without causing plunger assembly 42 movement around the first longitudinal axis A relatively to the distal rim 120, which is inserted into the body 111 and cannot be rotated relatively to the body 111. Of course, different constructions for providing an application device with a rotatable handle are possible.

FIG. 7f shows a perspective view of the syringe assembly 100 of FIGS. 7a, 7b, 7c, 7d and 7e with the handle 13 in a non-rotated position, wherein in FIG. 7g the syringe assembly 100 is illustrated in a state with the handle 13 rotated 90 degrees to the right relatively to the body 111. Thereby the syringe assembly 100 allows injections with injection angles α less than 15 degrees, in particular less than 12 degrees, with an ergonomic handling and therefore precise injections. In particular, handle orientation can be adjusted relatively to the mixing nozzle 12 and/or the body 11 to achieve optimal injection needle orientation respectively optimal bevel orientation of an injection needle connected to the mixing nozzle 12.

FIG. 8a to 8e show different views of the mixing nozzle 112 of the syringe assembly 100 of FIG. 7a to 7g.

FIG. 9a to 9e show different views of the syringe assembly 100 of FIGS. 7a to 7g without the mixing nozzle 112 and the plunger assembly 42 in a state as preferably provided in a kit according to the present invention, the further invention and/or the yet further invention, wherein the body 111 also comprises a proximal rim 134 for axial positioning of the mono-chamber syringes 24 and 15.

FIG. 10 shows a cross-sectional view of a fourth embodiment of a mixing nozzle 312 according to the present invention, wherein this mixing nozzle 312 additionally comprises a long static mixing element 345, extending parallel to the first longitudinal axis A for further improvement of mixing.

FIG. 11a shows a first perspective view of a fifth embodiment of a mixing nozzle 412 according to the present invention, wherein FIG. 11b shows a plan view of that mixing nozzle 412.

The second inlet channel segments 427B and 428B of both inlet channels 27 and 28 of this embodiment of a mixing nozzle 412 according to the present invention, extend almost linear in a plane perpendicular to the first longitudinal axis A.

Contrary to the mixing nozzles 12 and 112 and 212 described before, the mixing channel 422 of this mixing nozzle 412 does not comprise any flow manipulating elements, but is configured to change flow direction of a mixing flow at least partly alternating between at least a first flow direction and a second flow direction, wherein said mixing channel extends entirely, i.e. over its complete length, alternating at least in a first direction and a second direction, in particular zig-zag-shaped.

FIG. 12a shows a cross-sectional view of a detail of a third embodiment of syringe assembly 200 with a six embodiment of a mixing nozzle 512 according to the present invention and/or the yet further invention.

In this embodiment, according to the present invention and/or the yet further invention, the mixing nozzle 512 comprises a Luer-lock connector 219 as connection means 219, wherein in this embodiment the Luer-lock connector 219 is configured for being rotated around the first longitudinal axis A relatively to the body 211 respectively to a handle, which may be mounted non-rotatably to the body, to adjust needle orientation of an injection needle 247 fluid connected to the syringe assembly 200 by a corresponding Luer-lock connector 246 connected to the Luer-lock connector 219 of the syringe assembly 200.

For this purpose, i.e. for the rotation of the Luer-lock connector 219, in this embodiment the mixing nozzle 512 comprises a distal nozzle part 523A, a first proximal part 523B-1 and a second proximal nozzle part 523B-2, wherein the second proximal nozzle part 523B-2 is mounted to the first proximal nozzle part 523B-1 by an annular snap-fit connection 248 being configured to allow rotation of the first proximal nozzle part 223B-2 relative to the first distal nozzle part 523A around the first longitudinal axis A for adjusting needle orientation.

The second proximal nozzle part 523B-2 comprises a Luer-lock connector 219 for connecting the outlet channel 26 to an injection needle 247 having a lumen extending along a first longitudinal axis A and further comprises a corresponding Luer-lock connector 246, wherein the needle Luer-lock connector 246 is rotatable relatively to the Luer-cone of the Luer-lock connector 219 around the first longitudinal axis A.

For sealing purposes, the mixing nozzle 512 comprises at least one O-ring 251 as sealing means, arranged between the second proximal nozzle part 523B-2 and the first proximal nozzle part 523B-1.

FIG. 12b shows the syringe assembly 200 of FIG. 12a with connected injection needle 247 in injection position for intradermal injection into a human skin with an injection angle a of 10 degrees relative to a skin surface 250 for injection of a dermal filler composition comprising a first liquid composition and a second liquid composition capable of forming an in situ crosslinkable dermal filler composition, wherein in FIG. 12a the syringe assembly 200 is illustrated in a state with non-adjusted needle orientation, see FIG. 12c.

FIG. 12c illustrates in zoom view the injection needle's tip (bevel) 249 of the injection needle 247 of FIG. 12b in injection position with non-adjusted needle orientation relative to the skin surface 250. With this syringe assembly 200 according to the present invention and the yet further invention, optimal needle orientation for intradermal injection as illustrated in FIGS. 12d and 12e can be achieved by only rotating, i.e. turning, the Luer-lock connector 219 around the first longitudinal axis A relatively to the body 211 and the handle 213 until optimum needle orientation is reached. This will make it possible to avoid increasing of the injection angle due to package demands for rotating the handle 213. Hence, the syringe assembly 200 enables intradermal injection in a simple manner and precise application of discrete amounts of material.

It is known, that "needle orientation", i.e. the orientation of the bevel 249 preferably at the time of access or puncture during injection procedure, has at least an influence on pain, insertion forces, tissue deformation and tissue trauma. Therefore, using a syringe assembly 200 respectively a mixing nozzle 512 according to the present invention and/or the according to the further invention, allows one to achieve improved injection.

FIG. 13 illustrates an explosion view of a fourth embodiment of an application device 300 according to the present invention and/or according to the yet further invention with a seventh embodiment of a mixing nozzle 612 according to the present invention. Similar to the other embodiments of application devices 10, 100 and 200 described above, the application device 300 also comprises a body 311 having a window 318, a handle 313, a plunger assembly comprising plunger rods 314 with pistons 30 mounted thereto and a thumb plate 315, wherein in a state before use the plunger assembly can be locked by a clip 316. The body 311 is also configured for receiving two mono-chamber syringes 24, 25 (see FIG. 14) each having a body 24A, 25A and a tip 24B, 25B with a Luer connector as connection means, wherein the body 311 in particular is configured for receiving two mono-chamber syringes 24, 25 each being prefilled with a liquid composition, wherein the tips 24A, 24B of the two mono-chamber syringes 24, 25 are each closed by a cap 35, 36.

In contrast to the embodiments of application devices 10, 100, 200 described above, the plunger assembly of application device 300 is assembled of separate parts, in particular of a separate thumb plate 315 and separate plunger rods 314. Preferably, the plunger rods 314 are each connected to the thumb plate 315 by a snap-fit connection. In a preferred embodiment, in particular for securing the connection between the plunger rods 314 and the thumb plate 315, plunger rods 314 and thumb plate 315 may alternatively or additionally to the snap-fit connection be joined by welding, heat staking or gluing.

Furthermore, the application device 300 additionally comprises a mono-chamber syringe holder 357 (see also FIG. 15) wherein the mono-chamber syringe holder 357 comprises a connecting portion 360 being configured for acting as distal rim (see parts 20 and 120 of the application devices 10 and 100 in FIGS. 1a, 1d, 5a and 5d and, respectively, FIGS. 7a, 7d, 9a and 9d). The connecting portion 360 comprises two passage openings 364, one for each mono-chamber syringe 24, 25 to be hold by said holder 357. Further, the holder 357 comprises a longitudinal guiding portion extending parallel to the first longitudinal axis of the application device 300 in an assembled state having a scale 356 being visible through the window 318 of the body 311. For coupling the holder 357 to the handle 313, the application device 300 further comprises an O-Ring 361, which can be placed within the handle 313 (see FIG. 14). Preferably, on a distal side of the handle 313 further stickers 362 with instructions for use or annotations for use can be applied.

Figure 14:
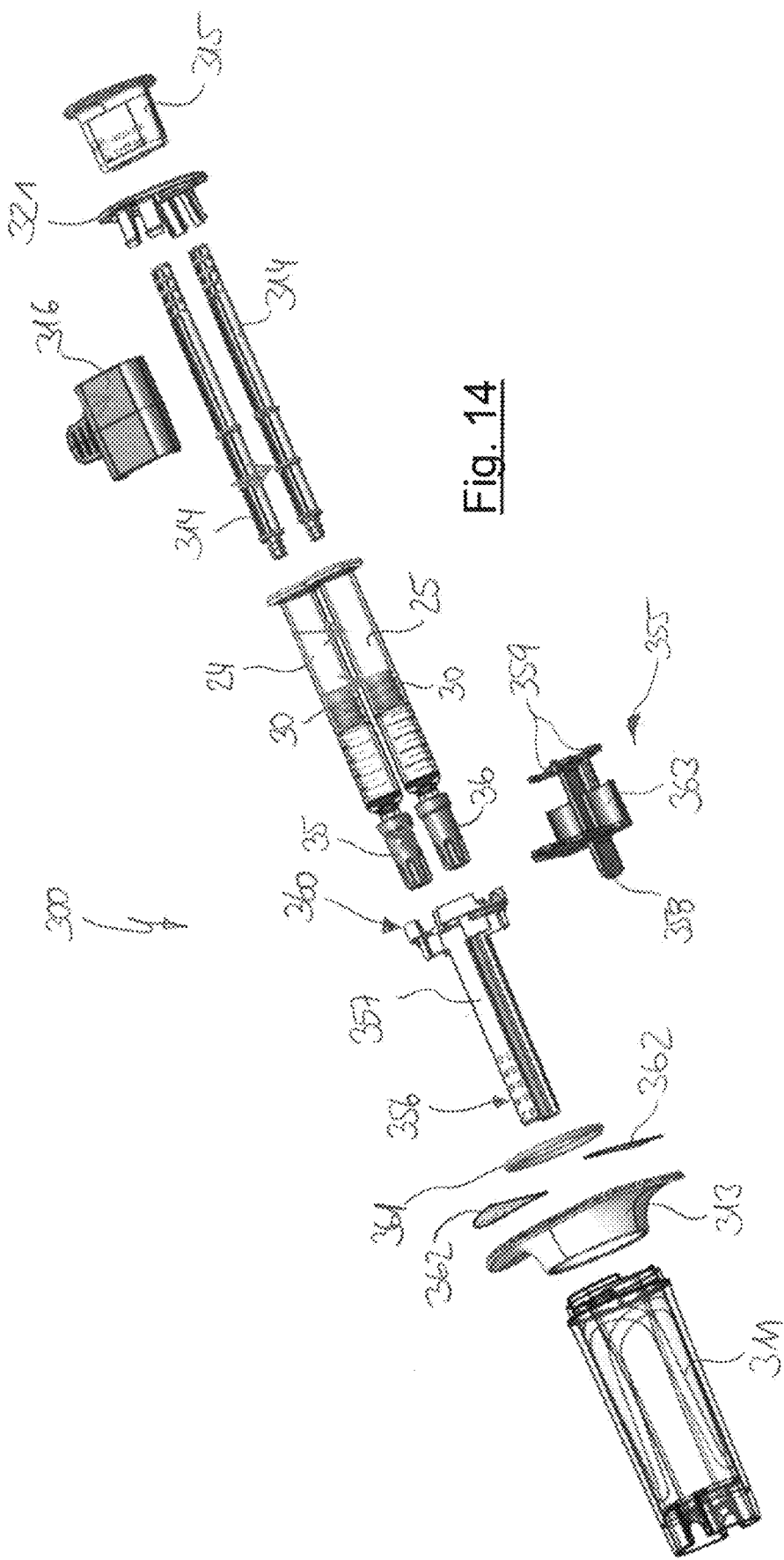
Figure 19:
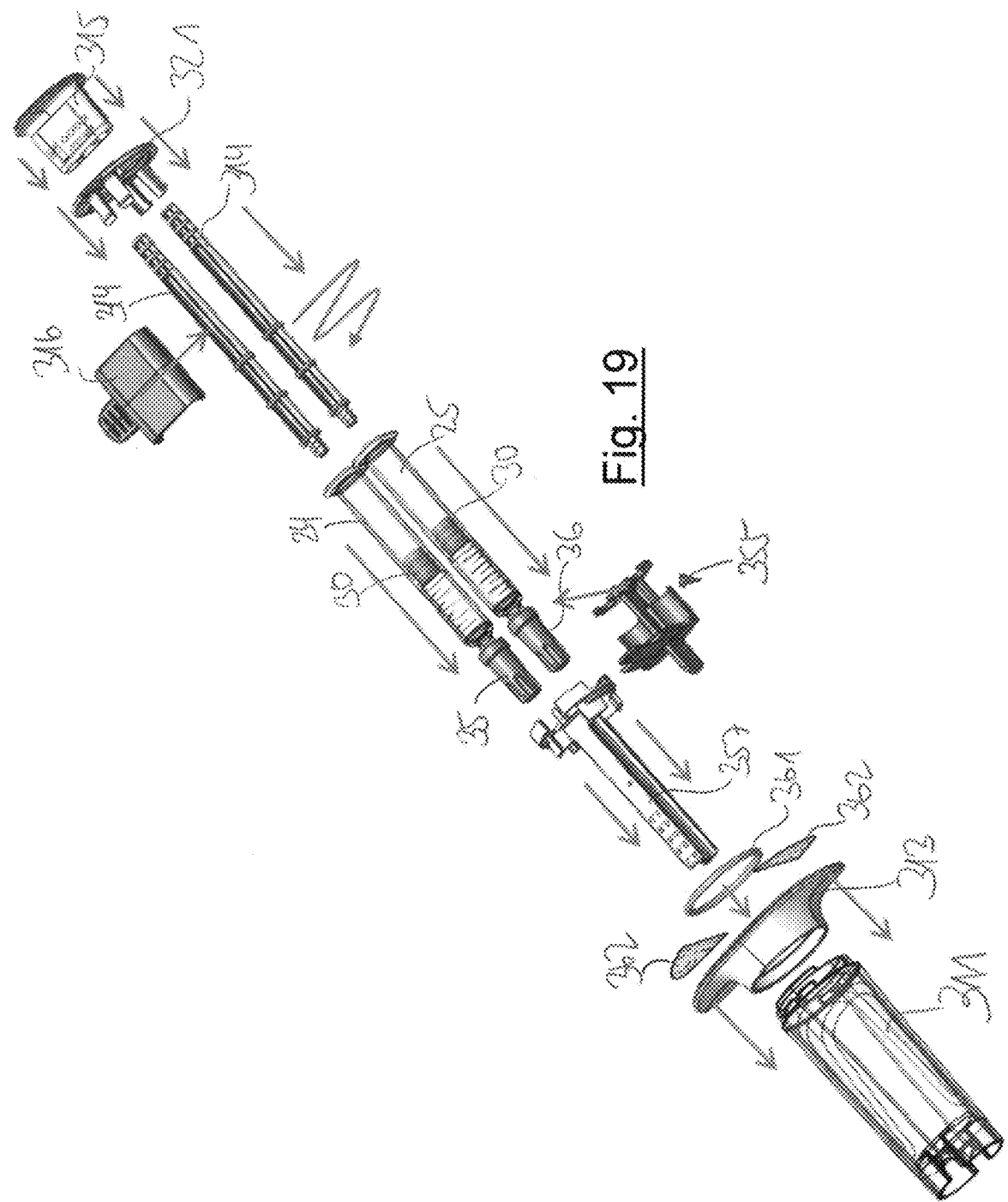

In some embodiments of an application device according the present invention and/or according to the yet further invention, the O-Ring 361 may be manufactured separately from handle 313 as illustrated in FIGS. 14 and 19. In other embodiments, the O-Ring 361 may be co-extruded as a TPE-part directly to the handle 313 or may be manufactured by two-component injection molding integrally with the handle 313. Thereby, the total numbers of individual parts to be assembled can be reduced, at least by one. As a consequence, the number of part handlings, assembly steps, logistic efforts and/or costs can be reduced.

As shown in FIG. 16, which illustrates the backstop plate 321 of the application device 300 of FIGS. 13 and 14 in a perspective view in detail, application device 300 also comprises different retaining means 321 in comparison to the embodiments described above. This backstop plate 321 of application device 300 comprises four clips 365 for mounting said backstop plate 321 via a snap-fit connection to the body 311 of the syringe assembly for securing the position of holder 357 together with the two mono-chamber syringes 24 and 25 within the body 311.

In addition to the application devices 10, 100 and 200 described above, for providing the application device 300 as a kit with body 311 and mixing nozzle 612 being disassembled, further a tip cap remover 355 can be coupled to the two mono-chamber syringes 24 and 25, which allows removing of the two caps 35, 36 simultaneously, see e.g. FIGS. 13, 14 and 17. FIG. 17 illustrates the tip cap remover 355 of the application device 300 in a perspective view in detail. By removing the tip caps 35 and 36 simultaneously, contamination of the first Luer connector 24B after removing the first cap 35 of mono-chamber syringe 24 during removing the second cap 36 can be avoided respectively vice versa. For coupling to the mono-chamber syringes 24, 25 the tip cap remover 355 comprises two clamps 359 and a flap 366, which can be locked in closing-position by a snap-fit connection. For easy cap removing, the tip cap remover 355 further comprises a (finger) grip 358.

FIG. 18a illustrates the seventh embodiment of the mixing nozzle 612 of the application device 300 of FIGS. 13 and 14 in an explosion view in detail. Similar to the second embodiment of an application device 100 according to the present invention being illustrated in FIGS. 7a to 9e, the mixing nozzle 612 can be releasably detached by a snap-fit connection to the body 311 of the application device 300, wherein the actuation means 617 for releasing said snap-fit connection are also arranged in the mixing nozzle 612. However, and in difference to mixing nozzle 112 illustrated in FIGS. 7a to 8e, this mixing nozzle 612 comprises at least three nozzle parts 623A, 623B-1 and 623B-2, namely a distal nozzle part 623A, a first proximal nozzle part 623B-1 and a second proximal nozzle part 623B-2, wherein the distal nozzle part 623A and the first proximal nozzle part 623B-1 of the mixing nozzle 612 are configured to be joint by welding, in particular by ultrasonic welding, and wherein the second proximal nozzle part 623B-2 can be mounted to the first proximal nozzle part 623B-1 and the distal nozzle part 623A by a snap-fit connection, in particular by the same snap-fit connection, which preferably cannot be released non-destructively.

For assembling the mixing nozzle 612 in a first step preferably, distal nozzle part 623A and first proximal nozzle part 623B-1 are joint to a subassembly, in particular by welding or heat staking or gluing, and in a further step, in particular in a subsequent step, the second proximal nozzle part 623B-2 is mounted to said subassembly by the snap-fit connection, wherein preferably said snap-fit connection cannot be released non-destructive.

In this embodiment, said snap-fit connection comprises actuation means 617, locking hooks 653 and a locking protrusion (undercut) 654 for establishment of the snap-fit connection between distal nozzle part 623A and first proximal nozzle part 623B-1 and is configured for connecting the nozzle parts 623A, 623B-1 and 623B-2 such that the locking hooks 653 will be hold in a locking position by the second proximal nozzle part 623B-2 after the second proximal nozzle part 623B-1 has been mounted to the subassembly, wherein for holding the locking hooks 653 in said locking position the second proximal nozzle part 623B-2 interacts with actuation mechanism 617.

In this embodiment of a mixing nozzle 612 according to the present invention illustrated in FIG. 18a, the actuation means 617 are further configured for connecting the mixing nozzle 612 detachably to a body of an application device via a snap-fit connection, in particular for connecting the mixing nozzle 612 to a body of an application device according to the present invention or according to the yet further invention. That means, both snap-fit connections (the snap-fit connection for connecting the nozzle parts 623A, 623-B1 and 623-B2 and the snap-fit connection for releasable detaching the mixing nozzle to the body 311 of the application device 300) are coupled, in particular operatively connected, wherein in the embodiment presented in FIG. 18a their actuation means 617 are coupled. Thereby, a package-saving connection between the mixing nozzle 612 and corresponding body of an application device can be realised.

This mixing nozzle 612 also comprises a mixing zone 629 with a mixing channel 622, an outlet channel 626, connection means 619, particularly a Luer-lock-connector 619, for connecting an injection needle (not shown) to the mixing nozzle 612, wherein in an established connection between the mixing nozzle 612 and the injection needle the outlet channel 626 of the mixing nozzle 612 is fluidly connected to a lumen of the injection needle.

For ease of manufacturing, in particular for ease of injection molding of the distal nozzle part 623A and the first proximal nozzle part 623B-1, the joint of the nozzle in the area of the mixing zone 629 is also arranged at least partly within the mixing zone 629, wherein the mixing zone 629 also extends in a plane perpendicular to the first longitudinal axis A.

As illustrated in FIG. 18b the mixing nozzle connection means 39, 40 of mixing nozzle 612 comprise an elastomeric material, in particular TPE for an optimized sealing between the first segments of the inlet channels 627A and 628A and the outlet channels of the mono-chamber syringes 24 and 25 (see FIGS. 13 and 14), wherein the inner surfaces of said connection means 39, 40, in particular the surfaces defining the Luer connector, are preferably overmolded with said elastomeric material, which is less stiff and less rigid compared to ABS the rest of the distal nozzle part 623A is made of. In alternative embodiments, the mixing nozzle connection means 39, 40 may comprise rubber, wherein the rubber material may be applied by vulcanizing to the distal nozzle part 623A.

FIG. 18c shows a bottom view of the distal nozzle part 623A of the mixing nozzle 612 of FIGS. 18a and 18b. In this view, in the design respectively the mixing geometry of the mixing zone 629, in particular of the mixing channel 622, is shown.

This seventh embodiment of a mixing nozzle 612 according to the present invention also comprises two inlet channels, each having first segments 627A, 628A extending in a direction parallel to the first longitudinal axis A and second segments 627B, 628B extending in a plane perpendicular to the first longitudinal axis A, wherein the second inlet channel segments 627B, 628B are slightly arc-shaped.

This seventh embodiment of a mixing nozzle 612 according to the present invention further comprises a mixing channel 622 extending in a plane perpendicular to the first longitudinal axis A, wherein a first segment 622A and a third segment 622C of said mixing channel 622 each extend in radial direction to said the first longitudinal axis A. A second segment 622B extends, according to a variant of the present invention, along a hexagonal contour, in particular along a contour of a hexagon with edges having an equal length, wherein in this seventh embodiment the second segment 622B of the mixing channel 622 extends over almost 5 edges of a hexagon defining the hexagonal contour.

FIGS. 19 and 20a to 20i illustrate several steps of a method of assembling the application device 300 according to a further aspect of the present invention before the mixing nozzle 612 will be connected to the body 311.

Figure 20D:
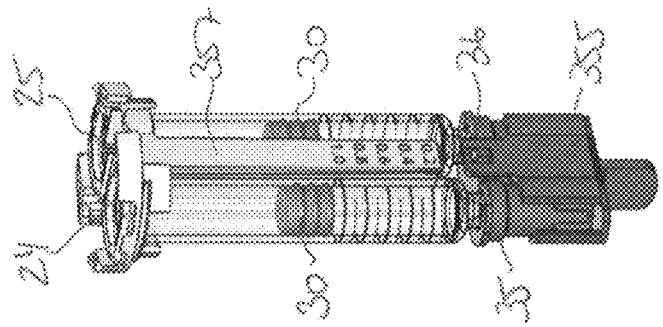
Figure 20C:
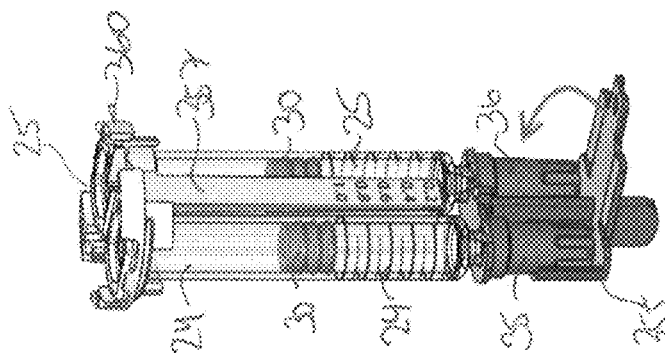
Figure 20B:
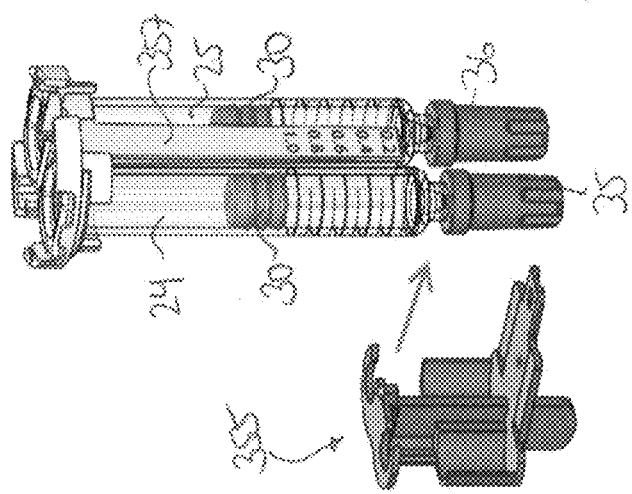
Figure 20A:
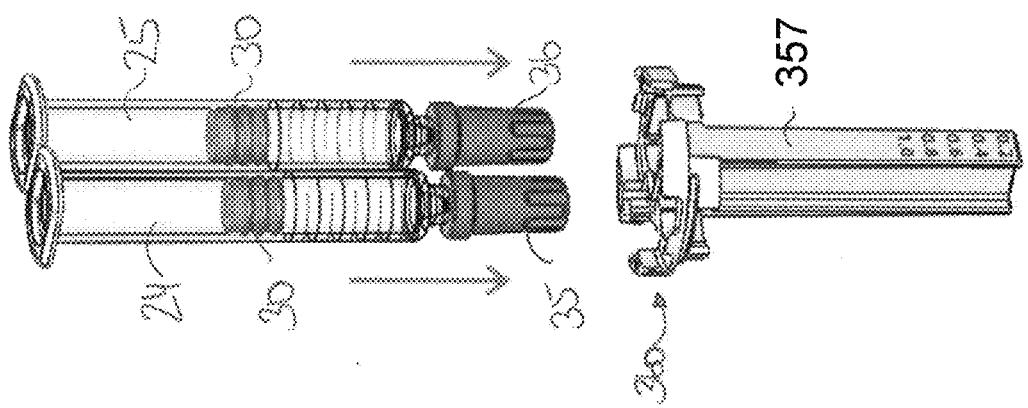

In a first or a further step, two separate, prefilled mono-chamber syringes 24, 25 (without plunger rods but with tips 24B and 25B each being covered by a tip cap 35, 36), wherein in particular one of the mono-chamber syringes 24 and 25 is prefilled with the first liquid composition LC1 and the other one with the second liquid composition LC2, are mounted to the holder 357 by plugging through the passage openings 364 of said holder 357 along the first longitudinal axis (see FIG. 20a).

In a first or a further step, the tip cap remover 355 is coupled to the mono-chamber syringes 24 and 25, in particular by arranging the Luer connectors 24B and 25B in the clamps 359 (see FIG. 17), closing the flap 366 of said tip cap remover 355 and securing said flap 366 by a snap-fit connection (see FIG. 20b to 20d) in the closing position.

In a further step, the assembly comprising the mono-chamber syringes 24, 25, holder 357 and the tip cap remover 355 is inserted into the syringe body 311 (see FIG. 20e), preferably after an O-Ring 361 has been placed within the handle 313 (see FIG. 19), wherein preferably the handle 313 is already coupled to the body 311 and wherein preferably stickers 362 with instructions for use or annotations for use are also already placed on the distal side of said handle 313 (see also FIG. 19)

For other embodiments comprising an O-Ring 361 manufactured integrally with the handle 313, the step of placing the O-ring 361 within the handle 313 is not necessary.

In a first or a further step, the plunger rods 314 are introduced at least partly into the mono-chamber syringe bodies 24A, 24B parallel to the first longitudinal axis and are connected, in particular screwed, to the pistons 30, which are already arranged in said mono-chamber syringes 24, 25 (see FIG. 20f).

In a further step, the backstop plate 321 is mounted at least to the handle 313 (see FIG. 20h).

In a further step thumb plate 315 is connected to the plunger rods 314, in particular by snap-fit connections (see FIG. 20h). To secure the connection between the plunger rods 314 and the thumb plate 315 a welding, heat staking or gluing step can be introduced.

In a further step, clip 316 is mounted to the plunger rods 314 for locking the plunger assembly and to avoid unintentional moving of said plunger assembly.

Figure 21B:
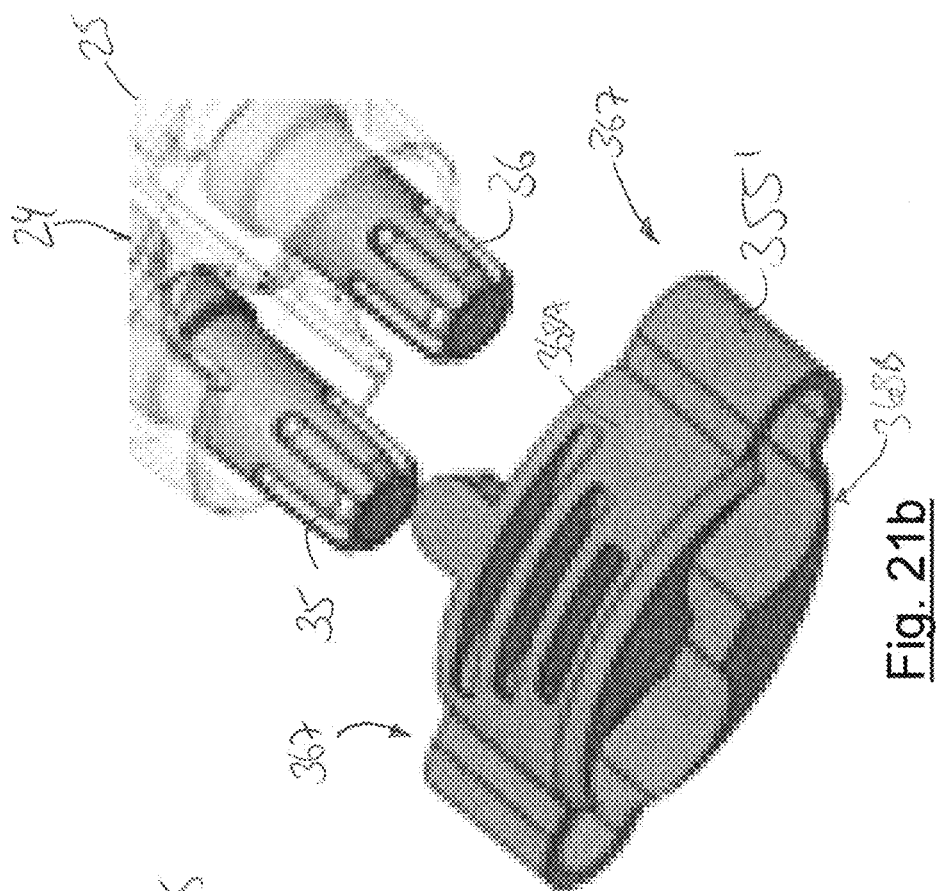
Figure 21A:
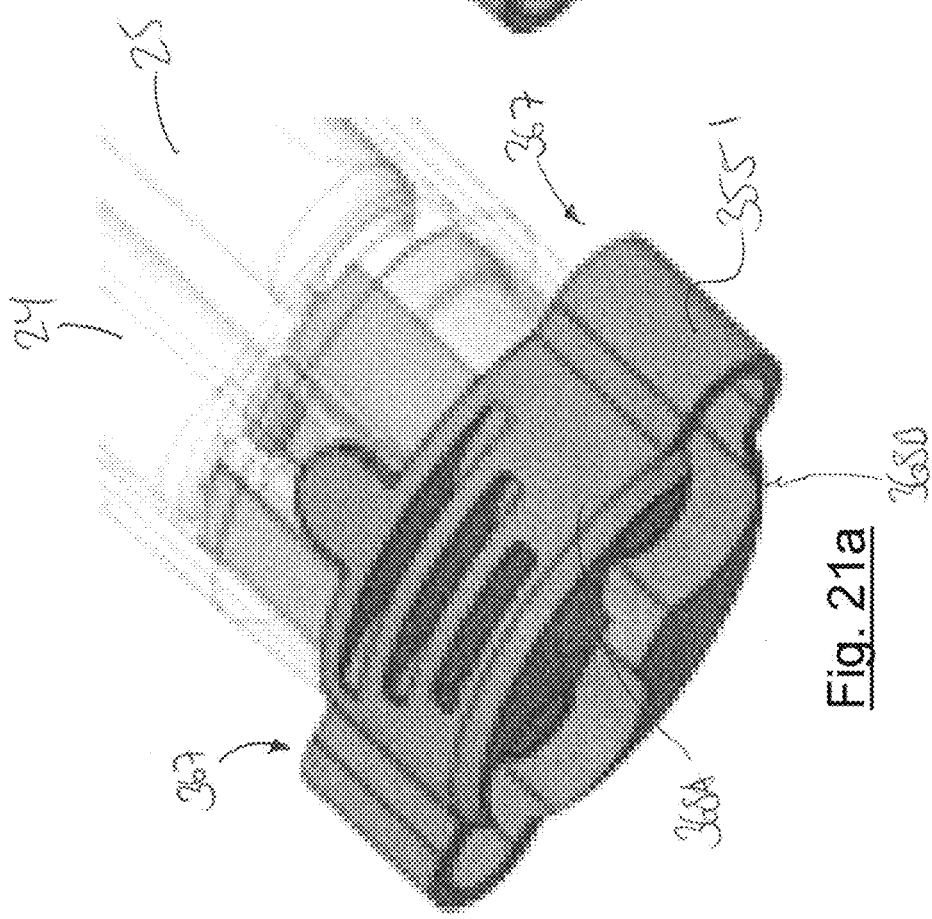

FIGS. 21a and 21b show a further embodiment of a tip cap remover 355', wherein FIG. 21a illustrates the tip cap remover 355' in a state being coupled to the caps 35, 36 of two mono-chamber syringes 24, 25 which are arranged in a body of an application device. FIG. 21b illustrates the tip cap remover 355' in a state before coupling to said caps 35, 36. This tip cap remover 355' also allows removing of the two caps 35, 36 simultaneously for avoiding contamination, wherein this tip cap remover 355' is configured such that it can be deformed elastically, preferably compressed elastically, by pressing the clamping means 368A and 368B towards each other by a user in a very easy manner for clamping the caps 35, 36 in between for grabbing and removing them simultaneously.

Therefore, the tip cap remover 355' comprises two flanges 367 made of an elastic material, in particular of an elastomeric material, e.g. of TPE or rubber or is comprising such an elastic material. Preferably, an inner surface of the tip cap remover 355' is configured for producing a sufficient friction for grabbing and removing the caps 35, 36. In a preferred embodiment of an application device or a kit according to at least one of the inventions described herein, if the tip cap remover is a tip cap remover 355' as illustrated in FIGS. 21a and 21b, the caps 35, 36 are made of or comprise TPE or rubber or a similar material for providing sufficient friction between the tip cap remover and the caps 35, 36 for removing.

In contrast to the tip cap remover 355 described in detail above, this tip cap remover 355' has not to be mounted to the mono-chamber syringes 24, 25 before inserting them into the body of an application device. It can be provided separately, in particular as an accessory and/or as a part of a kit according to the present invention.

FIGS. 22 to 28 illustrate several further mixing geometries of mixing zones 729, 829, 929, 1029, 1129, 1229, 1329 for further embodiments of a mixing nozzle according to the present invention.

FIG. 22 illustrates a bottom view of a further embodiment of a mixing geometry for a mixing nozzle according to the present invention, wherein this embodiment, compared to the mixing geometry depicted in FIGS. 18a and 18c, comprises a mixing zone 729 having a mixing channel 722 with second inlet channel segments 727B, 728B each extending circle arc-shaped around the first longitudinal axis A, in particular with an equal radius. In a further embodiment according to the present invention, additionally flow manipulating elements for changing flow direction may be arranged in the mixing channel, wherein preferably in the second segment 722B of said mixing channel flow manipulating elements are arranged, in particular alternating, in particular for alternating changing of flow direction.

FIG. 23 illustrates an embodiment of a mixing geometry for a mixing nozzle according to the present invention comprising a mixing zone 829 with a mixing channel 822 having a second segment 822B extending along a hexagonal contour over at least almost 5 edges of the hexagon defining said hexagonal contour, wherein the edges of the hexagon have different lengths. Second inlet channel segments 827B and 828B extend linear, in particular defining an angle in between of more than 90°. In a further embodiment according to the present invention, additionally flow manipulating elements for changing flow direction may be arranged in the mixing channel, wherein preferably in the second segment 822B of said mixing channel flow manipulating elements are arranged, in particular alternating, in particular for alternating changing of flow direction.

FIG. 24 illustrates an embodiment of a mixing geometry for a mixing nozzle according to the present invention comprising a mixing channel 922 having a second segment 922B extending circle arc-shaped to the first longitudinal axis A over more than 180° in circumferential direction, wherein within said mixing channel 922, in particular in the area of said second segment 922B of said mixing channel 922, flow manipulating elements 944 are arranged alternating for changing flow direction from a first flow direction to at least a second flow direction, in particular for changing flow direction alternatingly between a first flow direction and at least a second flow direction. The second inlet channel segments 927B and 928B also extend linear, in particular defining an angle in between of more than 90°.

FIG. 25 illustrates an embodiment of a mixing geometry for a mixing nozzle according to the present invention comprising a mixing channel 1022 having a second segment 1022B extending circle arc-shaped to the first longitudinal axis A in a first direction and in a second, opposite direction, extending over more than 180° in circumferential direction in both, first and second directions, wherein within said mixing channel 1022, in particular in the area of said second segment 1022B of said mixing channel 1022, also flow manipulating elements 1044 are arranged alternating for changing flow direction from a first flow direction to at least a second flow direction, in particular for changing flow direction alternatingly between a first flow direction and at least a second flow direction. The second inlet channel segments 1027B and 1028B also extend linear, in particular defining an angle in between of more than 90°.

FIG. 26 illustrates an embodiment of a mixing geometry for a mixing nozzle according to the present invention, which is similar to the embodiment illustrated in FIG. 25, wherein in the embodiment depicted in FIG. 26 a second segment 1122B of the mixing channel 1122 extends circle arc-shaped to the first longitudinal axis A in a first direction over 270° in circumferential direction and over 180° in circumferential direction in a second, opposite direction. The second inlet channel segments 1127B and 1128B each extend circle arc-shaped around the first longitudinal axis A, in particular with an equal radius.

Figure 27:
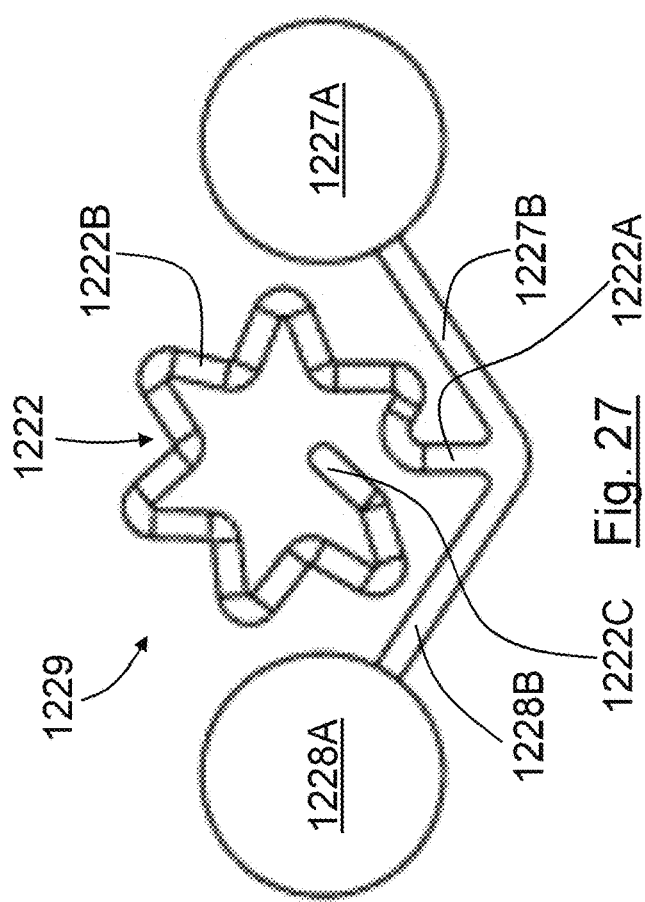

FIG. 27 illustrates an embodiment of a mixing geometry for a mixing nozzle according to the present invention comprising a mixing channel 1222 having a second segment 1222B extending along a star-shaped contour, in particular along a star-shaped contour of an 8-pointed star, wherein the second segment 1122B extends at least over 6 tips of the star defining the star-shaped contour. The second inlet channel segments 1227B and 1228B also extend linear, in particular defining an angle in between of more than 90°. In a further embodiment according to the present invention, additionally flow manipulating elements for changing flow direction may be arranged in the mixing channel, wherein preferably in the second segment 1222B of said mixing channel flow manipulating elements are arranged, in particular alternating, in particular for alternating changing of flow direction.

Figure 28:
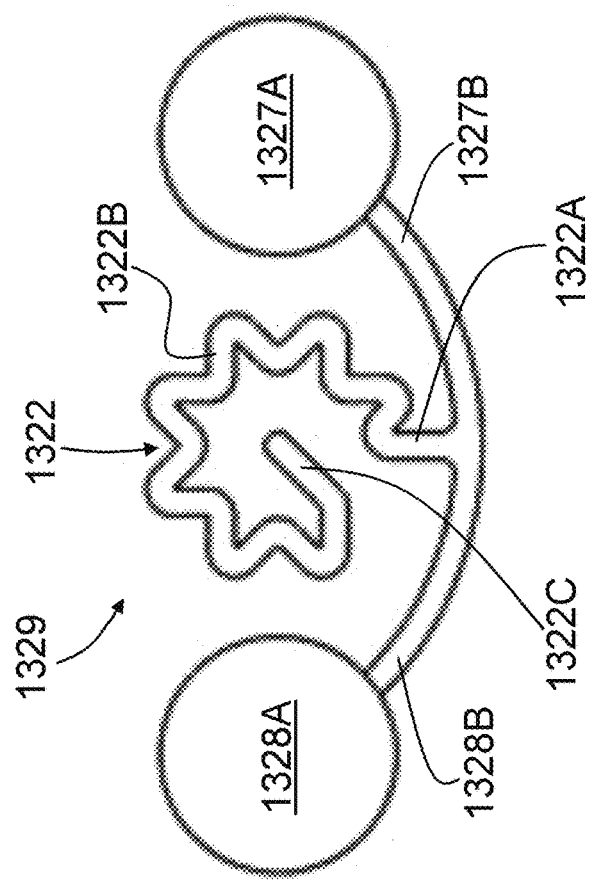

FIG. 28 illustrates an embodiment of a mixing geometry for a mixing nozzle according to the present invention comprising a mixing channel 1322 having a second segment 1322B also extending along a star-shaped contour, in particular along a star-shaped contour of a 8-pointed star, wherein in this embodiment the second segment 1322B extends at least over 7 tips of the star defining the star-shaped contour. The second inlet channel segments 1327B and 1328B each extend circle arc-shaped around the first longitudinal axis A, in particular with an equal radius. In a further embodiment according to the present invention, additionally flow manipulating elements for changing flow direction may be arranged in the mixing channel, wherein preferably in the second segment 1322B of said mixing channel flow manipulating elements are arranged, in particular alternating, in particular for alternating changing of flow direction.

LIST OF REFERENCE SIGNS 10 first embodiment of an application device according to the present invention and/or the further invention
100 second embodiment of an application device according to the present invention and/or the further invention
200 third embodiment of an application device according to the present invention, the further invention and/or the yet further invention
300 fourth embodiment of an application device according to the present invention, the further invention and/or the yet further invention
11, 111, 211, 311 body
12 first embodiment of a mixing nozzle according to the present invention
112 third embodiment of a mixing nozzle according to the present invention
212 second embodiment of a mixing nozzle according to the present invention
312 fourth embodiment of a mixing nozzle according to the present invention 412 fifth embodiment of a mixing nozzle according to the present invention
512 sixth embodiment of a mixing nozzle according to the present invention
612 seventh embodiment of a mixing nozzle according to the present invention
13, 213, 313 handle
13A upper part of the handle
13B lower part of the handle
14, 314 plunger rod
15, 315 thumb plate
16, 316 plunger rod locking means
17, 117, 217,617 actuation means for releasing snap-fit connection between mixing nozzle and body
18, 118, 318 window
19, 219, 619 connection means, Luer-lock connector
20, 120 distal rim
21, 321 retaining means (backstop plate)
22, 422, 622 722, 822, 922 1022, 1122, 1222, 1322 mixing channel
22A, 522A, 622A, 722A, 822A, 922A, 1022A, 1122A, 1222A, 1322A first segment of mixing channel
22B, 622B, 722B 822B, 922B, 1022B, 1122B, 1222B, 1322B second segment of segmented mixing channel
22C, 622C, 722C, 822C, 922C, 1022C, 1122C, 1222C, 1322C third segment of mixing channel
23A, 123A, 223A, 423A, 523A, 623A distal nozzle part
23B, 123B, 223B proximal nozzle part
24, 25 mono-chamber syringe (container)
24A, 25A mono-chamber syringe (container) body
24B, 25B mono-chamber syringe (container) tip with connection means (Luer-cone connector)
24C, 25C mono-chamber syringe flange
26, 626 outlet channel of the mixing nozzle
27 first inlet channel of the mixing nozzle
27A, 627A, 727A, 827A, 927A, 1027A, 1127A, 1227A, 1327A first, longitudinal extending segment of the first inlet channel of the mixing nozzle
27B, 427B, 527B, 627B, 727B, 827B, 927B, 1027B, 1127B, 1227B, 1327B second, arc-shaped segment of the first inlet channel of the mixing nozzle
28 second inlet channel of the mixing nozzle
28A, 628A, 728A, 828A, 928A, 1028A,1128A, 1228A, 1328A first, longitudinal extending segment of the second inlet channel of the mixing nozzle
28B, 428B, 528B, 628B, 728B, 8286,9286, 1028B, 1128B, 1228B, 1328B second, arc-shaped segment of the second inlet channel of the mixing nozzle
29, 229, 629, 729 829, 929, 1029, 1129, 1229, 1329 mixing zone
30 piston
31, 131,631 locking hook of the snap-fit connection between mixing nozzle and body
32, 132 locking protrusion (undercut) of the snap-fit connection between mixing nozzle and body
33 plunger locking hook
34, 134 proximal rim
35, 36 cap
37, 38 mono-chamber syringe (container) outlet channel
39, 40 mixing nozzle connection means (Luer-cone connector)
41 radial protrusions of sealing insert
42 plunger assembly
43 plunger tip with locking contour for snap-fit-connection to piston
44, 244, 944 1044, 1144 flow manipulating element
345 static mixing element
523B-1, 623B-1 first proximal nozzle part
523B-2, 623B-2 second proximal nozzle part
246 Luer-lock connector of an injection needle
247 injection needle
248 snap-fit connection
249 needle cut/bevel
250 skin surface
251 O-ring
252 nozzle joint
355, 355' tip cap remover
356 scale
357 mono-chamber syringe holder
358 grip
359 clamp
360 connecting portion configured as distal rim
363 cap holder
364 passage opening for mono-chamber syringe
365 clip
366 flap
367 flange
368A, 368B clamping means
653 locking hook of the snap-fit connection between distal nozzle part and first proximal nozzle part
654 locking protrusion (undercut) of the snap-fit connection between distal nozzle part and first proximal nozzle part
α injection angle
A first longitudinal axis
LC1 first liquid composition
LC2 second liquid composition

The invention claimed is:

1. A mixing nozzle for mixing at least a first liquid composition and a second liquid composition, the mixing nozzle being configured to be coupled to a body of a multi-component application device, optionally to a body of a two-component syringe assembly, for injection of a liquid composition, and said body being configured to separately store said at least first and second liquid compositions, wherein the mixing nozzle comprises:
at least two fluid inlet channels for receiving the separately stored liquid compositions to be mixed,
a mixing zone having at least one mixing channel for mixing the liquid compositions while they flow through the mixing channel, and
an outlet channel connectable to an injection needle having a lumen extending along a first longitudinal axis (A),
wherein said outlet channel of the mixing nozzle is fluidly connected or connectable with said inlet channels of the mixing nozzle by said mixing zone, and
wherein said mixing zone is configured to change flow direction of a mixing flow from a first flow direction at least to a second flow direction,
wherein said mixing channel
comprises flow manipulation elements arranged alternating within the mixing channel for changing flow direction, wherein the flow manipulation elements are designed as ramps and flow splitters which cause flow split and at least partly back flow,
and wherein said mixing channel
extends at least partly or entirely alternating at least in a first direction and a second direction, and/or
extends at least partly along an n-cornered contour, optionally along a hexagonal or an octagonal contour, and/or
extends at least partly along a star-shaped contour, wherein at least one of said at least two fluid inlet channels has at least one segment extending at least partly arc-shaped around said first longitudinal axis (A) in a plane perpendicular to said first longitudinal axis (A), wherein at least one of said mixing channels comprises at least a first segment and a second segment, wherein the segment extends at least partly or entirely in radial direction to said first longitudinal axis (A), and the second segment extends arc-shaped around said first longitudinal axis (A) in a plane perpendicular to said first longitudinal axis (A).

2. The mixing nozzle of claim 1, wherein the first segment of the mixing channel extending at least partly or entirely in radial direction runs at least partly meander-shaped, optionally in a plane parallel to said first longitudinal axis (A), and/or in a plane perpendicular to said first longitudinal axis.

3. The mixing nozzle of claim 1, wherein at least one of said mixing channels, optionally at least one of the at least first and second segments of the mixing channel, optionally said first segment and/or said second segment of the at least one mixing channel, extends at least partly or entirely in a plane perpendicular to said first longitudinal axis (A).

4. The mixing nozzle of claim 1, wherein the mixing nozzle comprises a Luer connector for connecting the injection needle to the mixing nozzle, wherein in an established connection between the mixing nozzle and said injection needle said outlet channel of the mixing nozzle is fluidly connected to a lumen of said injection needle, and wherein said Luer connector of the mixing nozzle is rotatable around said first longitudinal axis (A) to adjust needle orientation relative to the mixing nozzle and/or the application device.

5. The mixing nozzle of claim 1, wherein the mixing nozzle is assembled of at least a first part and a second part, wherein a joint between said first part and said second part passes at least partly through the mixing nozzle adjacent to said mixing channel or said mixing zone and/or at least partly within said mixing channel and/or said mixing zone.

6. A multi-component application device, optionally a two-component syringe assembly, for discharging a liquid mixed composition of at least a first liquid composition and a second liquid composition and for injection of the liquid mixed composition, the multi-component application device being configured to separately store in the application device the first and second liquid compositions and to mix the first and second liquid compositions before injection into a target site of a human body, wherein the application device comprises a mixing nozzle according to claim 1.

7. The multi-component application device of claim 6, wherein the application device comprises, in addition to the mixing nozzle, a body, a plunger assembly and a handle, wherein said handle optionally comprises two wings extending in opposite directions radially outwards from said body relating to said first longitudinal axis (A), and wherein said handle is rotatable around said first longitudinal axis (A) to adjust handle orientation relative to said mixing nozzle and/or said body.

8. The multi-component application device of claim 6, wherein said mixing nozzle is detachably mounted to said body, optionally by at least one snap-fit connection, wherein the application device optionally comprises at least one actuation means for releasing said snap-fit connection, wherein said actuation means is optionally arranged in said mixing nozzle or in said body, optionally in said body.

9. A method for cosmetic or therapeutic application, optionally for replacing or filling a biological tissue or increasing the volume of a biological tissue, wherein an effective amount of an injectable liquid composition, optionally an injectable dermal filler composition, is to be administered to a subject by using a multi-component application device according to claim 6 and/or a kit comprising said device.

10. A kit comprising a mixing nozzle according to claim 1, wherein the kit further comprises a first liquid composition A and a second liquid composition B (LC2), the first liquid composition A and the second liquid composition B optionally being capable of forming an in situ crosslinkable dermal filler composition, and wherein the first liquid composition A and the second liquid composition B are stored separately in the kit.

11. The kit of claim 10, wherein the first liquid composition A is a polysaccharide derivative functionalized with a first reactive group, optionally a nucleophilic group, and the second liquid composition B is a polysaccharide derivative functionalized with a second reactive group, optionally an electrophilic group, and wherein the first reactive group and the second reactive group are capable of forming covalent bonds between each other.

12. The kit of claim 10, wherein the kit comprises a multi-component application device, optionally a two-component syringe assembly, for discharging a liquid mixed composition of at least a first liquid composition and a second liquid composition and for injection of the liquid mixed composition, the multi-component application device being configured to separately store in the application device the first and second liquid compositions and to mix the first and second liquid compositions before injection into a target site of a human body.

13. The kit of claim 12, wherein the multi-component application device is a two-component syringe assembly for discharging a liquid mixed composition of a first liquid composition and a second liquid composition and for injection of the liquid mixed composition, the two-component syringe assembly comprising two barrels for storing the first and second liquid composition, each of the barrels having a Luer connector being configured for being coupled to the mixing nozzle.

14. The kit of claim 13, wherein the kit further comprises two tip caps and a tip cap remover, wherein the two tip caps each are covering at least partly one of the Luer connectors, and wherein the tip cap remover is configured for removing the two tip caps simultaneously.

15. The kit of claim 14, wherein the tip cap remover comprises two clamps and a flap, which can be locked in closing-position by a snap-fit connection, wherein the tip cap remover optionally further comprises a grip.

16. The kit of claim 14, wherein the tip cap remover comprises clamping means and is configured such that the remover can be deformed elastically, optionally compressed elastically, by pressing the clamping means towards each other by a user for clamping the caps in between for grabbing and removing them simultaneously.

* * * * *